(12) United States Patent
Frunzi et al.

(10) Patent No.: US 11,564,918 B2
(45) Date of Patent: Jan. 31, 2023

(54) PHARMACEUTICAL RESINATE COMPOSITIONS AND METHODS OF MAKING AND USING THEREOF

(71) Applicant: RHODES PHARMACEUTICALS L.P., Coventry, RI (US)

(72) Inventors: Gerard P. Frunzi, Garden City, NY (US); Sibao Chen, East Greenwich, RI (US); Rajeev A. Jain, Framingham, MA (US)

(73) Assignee: RHODES PHARMACEUTICALS L.P., Coventry, RI (US)

( * ) Notice: Subject to any disclaimer, the term of this patent is extended or adjusted under 35 U.S.C. 154(b) by 0 days.

(21) Appl. No.: 16/340,812

(22) PCT Filed: Oct. 10, 2017

(86) PCT No.: PCT/US2017/055878
§ 371 (c)(1),
(2) Date: Apr. 10, 2019

(87) PCT Pub. No.: WO2018/071381
PCT Pub. Date: Apr. 19, 2018

(65) Prior Publication Data
US 2019/0262334 A1    Aug. 29, 2019

Related U.S. Application Data

(60) Provisional application No. 62/406,134, filed on Oct. 10, 2016.

(51) Int. Cl.
| | |
|---|---|
| *A61K 31/485* | (2006.01) |
| *A61K 47/32* | (2006.01) |
| *A61P 29/02* | (2006.01) |
| *A61K 9/14* | (2006.01) |
| *A61K 9/16* | (2006.01) |
| *A61K 9/20* | (2006.01) |
| *A61K 31/78* | (2006.01) |

(52) U.S. Cl.
CPC ............ *A61K 31/485* (2013.01); *A61K 9/141* (2013.01); *A61K 9/16* (2013.01); *A61K 9/2027* (2013.01); *A61K 9/2054* (2013.01); *A61K 31/78* (2013.01); *A61K 47/32* (2013.01); *A61P 29/02* (2018.01)

(58) Field of Classification Search
None
See application file for complete search history.

(56) References Cited

U.S. PATENT DOCUMENTS

| | | |
|---|---|---|
| 6,375,957 B1 | 4/2002 | Kaiko et al. |
| 8,883,213 B2 | 11/2014 | Hall et al. |
| 2004/0091529 A1 | 5/2004 | Edgren et al. |
| 2013/0230587 A1 | 9/2013 | Pilgaonkar et al. |
| 2014/0127300 A1* | 5/2014 | Tengler ............... A61K 9/5031 424/487 |
| 2014/0127306 A1 | 5/2014 | Mehta et al. |
| 2015/0030677 A1 | 1/2015 | Adjei et al. |
| 2016/0228429 A1 | 8/2016 | Oshlack et al. |
| 2016/0346274 A1* | 12/2016 | Vaka ...................... A61K 9/501 |
| 2017/0271835 A1 | 9/2017 | Fukui et al. |
| 2017/0312226 A1* | 11/2017 | Gumudavelli ....... A61K 31/485 |

FOREIGN PATENT DOCUMENTS

| | | |
|---|---|---|
| WO | 2008/150526 | 12/2008 |
| WO | 2011/107855 | 9/2011 |
| WO | 2013/119231 | 8/2013 |
| WO | 2016/094751 | 6/2016 |

OTHER PUBLICATIONS

Aberlite IRP69 Technical Data Sheet, 2006, pp. 1-5. (Year: 2006).*
International Search Report for International Application No. PCT/US17/055878 dated Jan. 9, 2019, 2 pgs.
International Search Report for International Application No. PCT/US2018/054830 dated Dec. 26, 2018, 2 pgs.
Extended European Search Report for European Application No. EP 17 85 967 dated May 4, 2020, 8 pgs.
Maincent, et al., "Recent advances in abuse-deterrent technologies for the delivery of opioids," International Journal of Pharmaceutics, Jun. 2016, pp. 57-72 vol. 510, No. 1, Elsevier, NL.
Raval, et al., "Formulation and evaluation of tramadol hydrochloride mouth dissolving tablet," Journal of Global Pharma Technology, Jan. 1, 2010, pp. 17-22, vol. 2, No. 11.

* cited by examiner

*Primary Examiner* — Brian Gulledge
(74) *Attorney, Agent, or Firm* — Lowenstein Sandler LLP

(57) ABSTRACT

Disclosed herein are pharmaceutical compositions having a mixture of at least one active agent and an ion exchange resin, such that the composition releases about 75% or more of the at least one active agent within about 1 hour as measured by in-vitro dissolution in a USP Apparatus 2 (paddle) at about 50 rpm in about 900 ml 0.1N HCl at about 37° C. and related methods. Also disclosed herein are pharmaceutical compositions having a mixture of a drug susceptible to abuse, a non-opioid analgesic and an ion exchange resin, the composition further including at least one gelling agent and related methods.

24 Claims, 13 Drawing Sheets

PHARMACEUTICAL RESINATE COMPOSITIONS AND METHODS OF MAKING AND USING THEREOF

CROSS-REFERENCE TO RELATED APPLICATION(S)

This application is a national stage entry of PCT Application No. PCT/US2017/055878, filed Oct. 10, 2017, which claims priority to Provisional U.S. Application No. 62/406,134, filed Oct. 10, 2016, the contents of which are hereby incorporated by reference in their entirety.

FIELD

The present disclosure relates to pharmaceutical compositions which are resistant to tampering and abuse.

BACKGROUND

Pharmaceutical products may be subject to abuse. An individual seeking to abuse a pharmaceutical product may tamper with it in order to extract the active agent contained therein and administer the active agent in a more potent form for abuse. For example, a dose of opioid agonist may be more potent when administered parenterally as compared to the same dose administered orally. Methods of tampering with pharmaceutical products containing opioid agonists intended for oral administration may include, as non-limiting examples, crushing the pharmaceutical product or immersing it in solvents (such as, as a non-limiting example, ethanol) to extract the opioid agonist and administer it in a more potent form (such as, as non-limiting examples, a form for nasal or parenteral administration).

Previous attempts to reduce the abuse potential associated with pharmaceutical products containing opioid analgesics have been made. For example, commercially available tablets sold under trade name TALWIN® NX by Sanofi-Winthrop in the United States contain a combination of an amount of pentazocine hydrochloride equivalent to 50 mg base and an amount of naloxone hydrochloride equivalent to 0.5 mg base. When taken orally, the amount of naloxone present in this combination has low activity and minimally interferes with the pharmacologic action of pentazocine. When given parenterally, however, this amount of naloxone has antagonistic action to narcotic analgesics such as pentazocine. Thus, the inclusion of naloxone may curb a form of misuse of pentazocine which may occur when the oral dosage form is solubilized and injected (i.e., parenteral misuse). As additional examples of a similar approach, a fixed combination therapy comprising tilidine hydrochloride hemihydrate and naloxone hydrochloride dihydrate is available in Germany (sold under tradename VALORON® N, Goedecke) and a fixed combination of buprenorphine and naloxone is available in New Zealand (sold under tradename TEMGESIC® NX by Reckitt & Colman).

A need continues to exist in the art for pharmaceutical compositions containing a drug susceptible to abuse that are resistant to parenteral and nasal abuse, however. In addition, in the case of opioid analgesics, a need continues to exist for tamper-resistant formulations that do not solely rely upon the inclusion of an antagonist to deter parenteral and nasal abuse.

SUMMARY

In at least one embodiment, the present disclosure provides a pharmaceutical composition such as a solid oral dosage form comprising at least one active agent which is tamper-resistant.

In at least one embodiment, the present disclosure provides a pharmaceutical composition such as a solid oral dosage form comprising at least one active agent which is less susceptible to parenteral abuse than other solid dosage forms.

In at least one embodiment, the present disclosure provides a pharmaceutical composition such as a solid oral dosage form comprising at least one active agent which is less susceptible intranasal abuse than other solid dosage forms.

In at least one embodiment, the present disclosure provides a pharmaceutical composition such as a solid oral dosage form comprising at least one active agent which is less susceptible to diversion than other solid dosage forms.

In at least one embodiment, the present disclosure provides methods of treating a disease or condition in human patients by administering a pharmaceutical composition such as a solid oral dosage form as disclosed herein to a patient in need thereof.

In at least one embodiment, the present disclosure provides methods of treating pain in human patients by administering to a human patient in need thereof a pharmaceutical composition such as a solid oral dosage form comprising at least one opioid analgesic while reducing the potential for its abuse.

In at least one embodiment, the present disclosure provides methods of preparing a pharmaceutical composition such as a solid oral dosage form comprising at least one active agent as disclosed herein.

In at least one embodiment, the present disclosure provides a use of a medicament (e.g., an opioid analgesic) in the manufacture of a tamper-resistant dosage form as disclosed herein for the treatment of a disease state (e.g., pain).

In at least one embodiment, the present disclosure provides a pharmaceutical composition comprising a complex of at least one active agent and an ion exchange resin, wherein the composition releases about 75% or more of the at least one active agent within about 1 hour as measured by in-vitro dissolution in a USP Apparatus 2 (paddle) at about 50 rpm in about 900 ml 0.1N HCl at about 37° C.

In at least one embodiment, the present disclosure provides a pharmaceutical composition comprising an admixture of at least one active agent and an ion exchange resin, wherein the composition releases about 75% or more of the at least one active agent within about 1 hour as measured by in-vitro dissolution in a USP Apparatus 2 (paddle) at about 50 rpm in about 900 ml 0.1N HCl at about 37° C.

In at least one embodiment, the present disclosure is directed to methods of treating a disease or condition, such as, as non-limiting examples, pain or attention deficit hyperactivity disorder (ADHD), comprising administering to a patient in need thereof a pharmaceutical composition comprising a complex of at least one active agent and an ion exchange resin, wherein the composition releases about 75% or more of the at least one active agent within about 1 hour as measured by in-vitro dissolution in a USP Apparatus 2 (paddle) at about 50 rpm in about 900 ml 0.1N HCl at about 37° C.

In at least one embodiment, the present disclosure provides methods of treating a disease or condition, such as, as non-limiting examples, pain or attention deficit hyperactivity disorder (ADHD), comprising administering to a patient in need thereof a pharmaceutical composition comprising an admixture of at least one active agent and an ion exchange resin, wherein the composition releases about 75% or more of the at least one active agent within about 1 hour as measured by in-vitro dissolution in a USP Apparatus 2 (paddle) at about 50 rpm in about 900 ml 0.1N HCl at about 37° C.

In at least one embodiment, the present disclosure is directed to methods of deterring abuse of a drug susceptible to abuse, comprising administering to a patient in need thereof a pharmaceutical composition comprising a complex of at least one active agent and an ion exchange resin, wherein the composition releases about 75% or more of the at least one active agent within about 1 hour as measured by in-vitro dissolution in a USP Apparatus 2 (paddle) at about 50 rpm in about 900 ml 0.1N HCl at about 37° C.

In at least one embodiment, the present disclosure is directed to methods of deterring abuse of a drug susceptible to abuse, comprising administering to a patient in need thereof a pharmaceutical composition comprising an admixture of at least one active agent and an ion exchange resin, wherein the composition releases about 75% or more of the at least one active agent within about 1 hour as measured by in-vitro dissolution in a USP Apparatus 2 (paddle) at about 50 rpm in about 900 ml 0.1N HCl at about 37° C.

In at least one embodiment, the present disclosure is directed to methods of preparing pharmaceutical compositions comprising forming a complex of at least one active agent and an ion exchange resin and incorporating the complex into a pharmaceutical composition, wherein the composition releases about 75% or more of the at least one active agent within about 1 hour as measured by in-vitro dissolution in a USP Apparatus 2 (paddle) at about 50 rpm in about 900 ml 0.1N HCl at about 37° C.

In at least one embodiment, the present disclosure is directed to methods of preparing pharmaceutical compositions comprising forming an admixture of at least one active agent and an ion exchange resin and incorporating the complex into a pharmaceutical composition, wherein the composition releases about 75% or more of the at least one active agent within about 1 hour as measured by in-vitro dissolution in a USP Apparatus 2 (paddle) at about 50 rpm in about 900 ml 0.1N HCl at about 37° C.

Definitions

In describing the present disclosure, the following terms are to be used as indicated below. As used herein, the singular forms "a," "an," and "the" include plural references unless the context clearly indicates otherwise. Thus, for example, reference to "an active agent" includes a single active agent as well as a mixture of two or more different active agents, and reference to "a resin" includes a single resin as well as a mixture of two or more different resins, and the like.

As used herein, the term "about" in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number ±10%, such that "about 10" would include from 9 to 11.

The term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that. In certain embodiments, the term "at least about" includes the recited number minus 10% and any quantity that is higher such that "at least about 10" would include 9 and anything higher than 9. This term can also be expressed as "about 10 or more." Similarly, the term "less than about" typically includes the recited number plus 10% and any quantity that is lower such that "less than about 10" would include 11 and anything less than 11. This term can also be expressed as "about 10 or less."

As used herein, the terms "active agent," "active ingredient," "pharmaceutical agent," and "drug" refer to any material that is intended to produce a therapeutic, prophylactic, or other intended effect, whether or not approved by a government agency for that purpose. These terms with respect to specific agents include all pharmaceutically active forms of the agent, including the free base form of the agent, and all pharmaceutically acceptable salts, complexes, stereoisomers, crystalline forms, co-crystals, ether, esters, hydrates, solvates, and mixtures thereof, where the form is pharmaceutically active.

The term "admixture," with respect to the at least one active agent and the ion exchange material, means that the two materials are at least partially dispersed within each other in the form of a physical mixture without chemical interaction.

The term "complex" with respect to the at least one active agent and the ion exchange material, means a material or mixture in which the at least one active agent and the ion exchange material chemically interact, such as, as a non-limiting example, via a chemical bond forming between the two materials, e.g., by covalent binding, ionic binding, van der Waals forces. In certain embodiments, 25% or more, 50% or more, 75% or more, 85% or more or 95% or more of the mixture comprises a complex of the at least one active agent and the ion exchange resin.

As used herein, the terms "therapeutically effective" refers to the amount of drug or the rate of drug administration needed to produce a desired therapeutic result.

As used herein, the terms "prophylactically effective" refers to the amount of drug or the rate of drug administration needed to produce a desired prophylactic result.

As used herein, the term "stereoisomers" is a general term for all isomers of individual molecules that differ only in the orientation of their atoms in space. It includes enantiomers and isomers of compounds with one or more chiral centers that are not mirror images of one another (diastereomers).

The term "enantiomer" or "enantiomeric" refers to a molecule that is nonsuperimposable on its mirror image and hence optically active wherein the enantiomer rotates the plane of polarized light in one direction by a certain degree, and its mirror image rotates the plane of polarized light by the same degree but in the opposite direction.

The term "chiral center" refers to a carbon atom to which four different groups are attached.

The term "racemic" refers to a mixture of enantiomers.

The term "resolution" refers to the separation or concentration or depletion of one of the two enantiomeric forms of a molecule.

The term "patient" means a subject, particularly a human, who has presented a clinical manifestation of a particular symptom or symptoms suggesting the need for treatment, who is treated preventatively or prophylactically for a condition, or who has been diagnosed with a condition to be treated. The term "subject" is inclusive of the definition of the term "patient" and does not exclude individuals who are entirely normal in all respects or with respect to a particular condition.

For purposes of this disclosure, "pharmaceutically acceptable salts" include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt and the like.

The term "ppm" as used herein means "parts per million."

The term "layered" means being completely or partially coated onto a substrate.

The term "bioavailability" means to the relevant extent to which the drug (e.g., oxycodone) is absorbed from the pharmaceutical composition such as a unit dosage form. Bioavailability also refers to the AUC (i.e., area under the plasma concentration/time curve).

The term "$C_{max}$" denotes the maximum plasma concentration obtained during the dosing interval.

The term "$T_{max}$" denotes the time to maximum plasma concentration ($C_{max}$).

The terms "population of patients," "population of subjects," and "population of healthy subjects" refer to the mean pharmacokinetic parameters of at least two patients, subjects, or healthy subjects; at least six patients, subjects or healthy subjects; or at least twelve patients, subjects or healthy subjects.

The term "substrate" means a substance or layer of a material. In at least one embodiment, the term "substrate" means an inert core. In at least one embodiment, the term "substrate" means a particle or granule, including, as a non-limiting example, a particle or granule containing an active agent different than or the same as the at least one active agent.

For purposes of the present disclosure, the formulations disclosed herein may be dose proportional. In dose proportional formulations, the pharmacokinetic parameters (e.g., AUC and $C_{max}$) and/or in-vitro release increase linearly from one dosage strength to another. Therefore, the pharmacokinetic and in-vitro parameters of a particular dose can be inferred from the parameters of a different dose of the same formulation.

DETAILED DESCRIPTION

Figure 1:
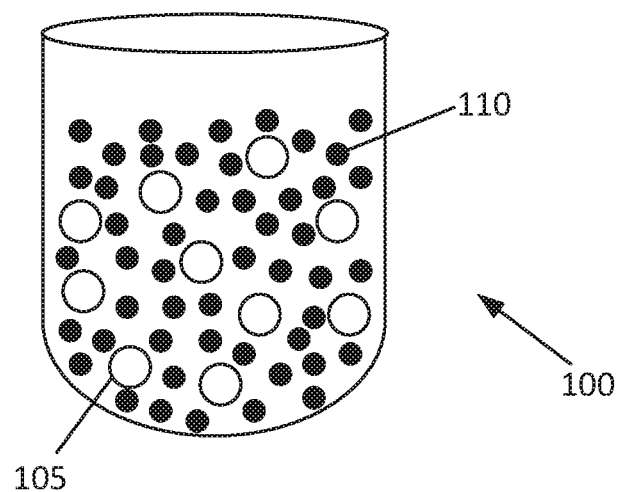
FIG. 1 is a graphical depiction of an exemplary pharmaceutical composition comprising an admixture of at least one active agent and an ion exchange material, formed in the absence of an aqueous medium, according to an exemplary embodiment of the present disclosure.

Pharmaceutical formulations may be the subject of abuse. As one example of a method used to abuse pharmaceutical formulations, a pharmaceutical product in solid dosage form is crushed in order to liberate the active agent contained therein and administer it, such as through parenteral administration or nasal administration (absorption across a mucosal surface), in a more potent form. As another example, a solid dosage form is dissolved (e.g., in an aqueous or non-aqueous solvent) to make a solution of the active agent that can be readily drawn into a syringe for parenteral administration.

Immediate-release dosage forms play a role in the management of both acute and chronic conditions (e.g., pain management with opioid analgesics). Therefore, tamper-resistant solid dosage forms of drugs susceptible to abuse must maintain an immediate-release profile when administered orally as prescribed.

In at least one embodiment, the present disclosure provides pharmaceutical compositions comprising at least one active agent and an ion exchange material which provides an immediate release of the at least one active agent when orally administered as prescribed, but which exhibits decreased dissolution of the at least one active agent when placed in a medium that does not mimic gastric fluid, e.g., an aqueous medium, an alcohol, a mixed alcohol, or a mixed alcohol/water medium. In such at least one embodiment, the at least one active agent and the ion exchange material form a complex such that the complex releases the at least one active agent at different rates upon exposure to different media. In another such at least one embodiment, the pharmaceutical composition comprises an admixture of at least one active agent and the ion exchange material, such that the at least one active agent and the ion exchange material form such a complex when the pharmaceutical composition is placed in a medium that does not mimic gastric fluid, e.g., an aqueous medium such as an alcohol or a mixed alcohol/water medium.

The present disclosure thus provides pharmaceutical compositions comprising a complex or an admixture of at least one active agent and an ion exchange material, wherein the pharmaceutical composition releases about 75% or more, about 85% or more, or about 95% or more of the at least one active agent within about 1 hour as measured by in-vitro dissolution in a USP Apparatus 2 (paddle) at about 50 rpm in about 900 ml 0.1N HCl at about 37° C. In at least one embodiment, the pharmaceutical compositions disclosed herein may release about 85% or more, about 92% or more, or about 98% or more of the active agent within about 30 minutes as measured by in-vitro dissolution in a USP Apparatus 2 (paddle) at about 50 rpm in about 900 ml 0.1N HCl at about 37° C.

When placed in an aqueous medium, however, the pharmaceutical compositions disclosed herein may exhibit decreased dissolution of the at least one active agent. For example, according to at least one embodiment, the pharmaceutical compositions disclosed herein may release about 20% or less of the at least one active agent within about 20 minutes as measured by in-vitro dissolution in a USP Apparatus 2 (paddle) at about 50 rpm in about 900 ml water at about 37° C. In certain embodiments, the pharmaceutical compositions disclosed herein may release about 20% or less, about 10% or less, or about 5% or less of the least one active agent within about 20 minutes as measured by in-vitro dissolution in a USP Apparatus 2 (paddle) at about 50 rpm in about 900 ml water at about 37° C. Moreover, in at least one embodiment, the pharmaceutical compositions disclosed herein may release about 30% or less, about 20% or less, or about 10% or less of the active agent within about 45 minutes as measured by in-vitro dissolution in a USP Apparatus 2 (paddle) at about 50 rpm in about 900 ml water at about 37° C.

Similarly, the pharmaceutical compositions disclosed herein may exhibit decreased dissolution of the at least one active agent when placed in an alcohol or mixed aqueous/alcohol medium. For example, the pharmaceutical compositions disclosed herein may release about 20% or less, about 10% or less, or about 5% or less of the at least one active agent within about 20 minutes as measured by in-vitro dissolution in a USP Apparatus 2 (paddle) at about 50 rpm in about 900 ml of about 40% alcohol in water (v/v) at about 37° C. In certain example embodiments, the composition may release about 30% or less, about 20% or less, or about 10% or less of the active agent within about 45 minutes as measured by in-vitro dissolution in a USP Apparatus 2 (paddle) at about 50 rpm in about 900 ml of about 40% alcohol in water (v/v) at about 37° C. A non-limiting example of an alcohol is ethanol.

This decreased dissolution of the at least one active agent in the pharmaceutical compositions disclosed herein when placed in aqueous media may be measured in terms of "syringeability." For purposes of the present disclosure, "syringeability" refers to the amount of the at least one active agent which may be extracted into a syringe of a particular gauge (e.g., 21G, 23G, 27G, 28G, 29G, 30G, 31G) through a cotton ball or other filter material from a mixture of the pharmaceutical composition and a solvent, relative to the total amount of the at least one active agent originally present in the pharmaceutical composition. Non-limiting examples of aqueous media which may be useful as solvents to test syringeability include 40% ethanol in water, saline, tap water, and vinegar, for instance. For example, the pharmaceutical composition may be intact, crushed or milled and dissolved in a small amount of solvent (e.g., 1 ml, 5 ml or 10 ml). The dissolution may take place with or without agitation (e.g., vigorous shaking, sonication, etc.) for a particular time period (e.g., 1 min, 2, min, 5 min, 10 min, or at least 1 min). Syringeability may be tested when the solvent is at room temperature or boiling (e.g., 95° C.), for example. In at least one embodiment, the percent of the at least one active agent extracted into a syringe from a mixture of a pharmaceutical composition as disclosed herein and an aqueous solvent may be 30% or less, relative to the total amount of the at least one active present in the pharmaceutical composition. In at least one embodiment, for example, the percent extracted may be 29% or less, 28% or less, 27% or less, 26% or less, 25% or less, 24% or less, 23% or less, 22% or less, 21% or less, 20% or less, 19% or less, 18% or less, 17% or less, 16% or less, 15% or less, 14% or less, 13% or less, 12% or less, 11% or less, 10% or less, 9% or less, 8% or less, 7% or less, 6% or less, 5% or less, 4% or less, 3% or less, 2% or less, or 1% or less.

Ion Exchange Materials

Ion exchange materials suitable for the pharmaceutical compositions disclosed herein are chosen from pharmaceutically acceptable ion exchange materials capable of associating or chemically interacting with at least one active agent either in solution or in situ to form a complex, such as a resinate, and releasing the at least one active agent when the complex is exposed to a release medium. Pharmaceutically acceptable ion exchange materials include any ion exchange material that is not toxic to animals such as humans, does not interfere substantially with the medicinal effect of an active agent associated with the ion exchange material, contains a pharmacologically inert matrix containing functional groups that are ionic or that are ionizable under certain conditions of pH, have a moisture content between 0% and the water retention capacity of the ion exchange material, and is minimally soluble or insoluble in water. In at least one embodiment, the ion exchange material, such as a resin, may be a macroporous or gel type resin. In general, ion exchange materials such as resins suitable for use in ion exchange chromatography or for applications such as deionization of water are suitable ion exchange materials in the pharmaceutical compositions disclosed herein. Examples of ion exchange materials, including resins, are described by H. F. Walton in "Principles of Ion Exchange" (pp. 312-343) and "Techniques and Applications of ion-Exchange Chromatography" (pp. 344-361) in Chromatography. (E. Heftmarm, editor), Van Nostrand Reinhold Company, New York (1975); Kitagawa, U.S. Pat. No. 6,218,440; Barby, U.S. Pat. No. 4,522,953; Dowex: Ion Exchange Resins. Fundamentals of Ion Exchange (2000); and Hughes, Ion Exchange Resins; Unique Solutions to Formulation Problems, Pharmaceutical Technology: Excipients and Solid Dosage Forms, pages 20-25 (June 2004). Examples of ion exchange materials other than resins are described in Hollenbeck, U.S. Patent Publication No. 2005/0013792. Other ion exchange materials, such as cross-linked sodium carboxymethyl cellulose and carbomers, such as those sold under the tradename CARBOPOL® (Noveon Inc., Cleveland, Ohio), may also be used. Additional examples of ion exchange materials other than resins are disclosed in Hollenbeck, U.S. Patent Publication No. 2005/0013792.

The ion exchange material or resin can be in an ionized form, a salt form, or a partial salt form, and can be cationic or anionic. Typically, a cationic ion exchange material is used with a positively charged active agent, and an anionic ion exchange material is used with a negatively charged active agent. Non-limiting examples of anionic exchange resins include, but are not limited to, at least one of styrenic, strongly basic anion exchange resins with a quaternary amine functionality; styrenic, weakly basic anion exchange resins with a primary, secondary, or tertiary amine functionality; acrylic or methacrylic strongly basic anion exchange resins with a quaternary amine functionality; acrylic or methacrylic weakly basic anion exchange resins with a primary, secondary, or tertiary amine functionality; and allylic, and vinylic weakly basic anion exchange resins with a primary, secondary, or tertiary amine functionality.

Examples of cationic exchange resins include, but are not limited to, at least one of styrenic, strongly acidic cation exchange resins with sulfonic or phosphonic acid functionality; styrenic, weakly acidic cation exchange resins with carboxylic or phenolic acid functionality; and acrylic or methacrylic weakly acidic cation exchange resins with a carboxylic or phenolic acid functionality.

According to various embodiments of the disclosure, the ion exchange resin can include a sulfonated copolymer of styrene and divinylbenzene. In certain embodiments, a suitable ion exchange resin can be the pharmaceutical grade cation exchange resin sold under trade name AMBERLITE™ IRP69 by Dow. Additional non-limiting examples of pharmaceutically acceptable ion exchange materials suitable for the pharmaceutical compositions disclosed herein include those sold under trade names AMBERLITE™ IRP476, AMBERLITE™ IRP64, and AMBERLITE™ IRP88 by Dow.

In at least one embodiment, the ion exchange material may comprise a partial potassium salt of a copolymer of methacrylic acid with divinyl benzene, such as, for example, polacrilin potassium. A non-limiting example of polacrilin potassium includes the product sold under trade name C115KMR by Purolite. Other non-limiting examples of pharmaceutically acceptable ion exchange materials suitable for the pharmaceutical compositions disclosed herein include those sold under trade names A430MR, C100CaMR, C100MRNS, C108DR, and C115HMR by Purolite.

In at least one embodiment disclosed herein, the ion exchange material is chosen from polacrilex resin, polacrilin salt, sodium polystyrene sulfonate, cholestyramine resin, and mixtures thereof.

In at least one embodiment disclosed herein, the ion exchange material is chosen from (i) sulfonated copolymers of styrene and divinylbenzene, (ii) methacrylic acid-divinyl benzene copolymers, and (iii) polystyrene resins having amine and/or ammonium side groups.

At Least One Active Agent

The at least one active agent in the pharmaceutical compositions disclosed herein may be chosen from, but not limited to, angiotensin-converting-enzyme (ACE) inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, anti-pyretics, anti-inflammatory agents, androgens, local and general anesthetics, anti-addictive agents, anti-androgens, anti-arrhythmic agents, antiasthmatic agents, anti-cholinergic agents, anti-cholinesterase agents, anti-coagulants, anti-diabetic agents, anti-diarrheal agents, anti-diuretic, anti-emetic agents, prokinetic agents, anti-epileptic agents, anti-estrogens, anti-fungal agents, anti-hypertensive agents, anti-microbial agents, anti-migraine agents, anti-muscarinic agents, anti-neoplastic agents, anti-parasitic agents, anti-parkinson's agents, antiplatelet agents, anti-progestins, anti-schizophrenia agents, anti-thyroid agents, antitussives, anti-viral agents, atypical anti-depressants, azaspirodecanediones, barbiturates, benzodiazepines, benzothiadiazides, beta-adrenergic agonists, betaadrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, cannabinoids, catecholamines and sympathomimetic drugs, cholinergic agonists, cholinesterase reactivators, central nervous system (CNS) depressants, stimulants such as CNS stimulants, contraceptive agents, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, hormones, 5-hydroxytryptamine antagonists, drugs for the treatment of hyperlipoproteinemia, hypnotics, sedatives, immunosuppressive agents, laxatives, methylxanthines, monoamine oxidase inhibitors, neuromuscular blocking agents, organic nitrates, opioid agonists, opioid antagonists, pancreatic enzymes, phenothiazines, progestins, prostaglandins, agents for the treatment of psychiatric disorders, psychotropics, retinoids, sedative hypnotics, sodium channel blockers, agents for spasticity and acute muscle spasms, succinimides, testosterones, thioxanthines, thrombolytic agents, thyroid agents, tricyclic antidepressants, inhibitors of tubular transport of organic compounds, tranquilizers, drugs affecting uterine motility, vasodilators, vitamins, and mixtures thereof.

In at least one embodiment, the at least one active agent is a drug susceptible to abuse, such as, for example, an opioid analgesic such as an opioid agonist. Non-limiting examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist may be selected from codeine, fentanyl, hydromorphone, hydrocodone, oxycodone, dihydrocodeine, dihydromorphine, morphine, tramadol, oxymorphone, pharmaceutically acceptable salts thereof, and mixtures thereof.

In various embodiments, the opioid agonist can be chosen from at least one of oxycodone, oxymorphone, hydrocodone, hydromorphone, morphine, codeine, tramadol, tapentadol, fentanyl, pharmaceutically acceptable salts, hydrates and solvates thereof or mixtures thereof. As non-limiting examples, pharmaceutically acceptable salts of opioid agonists include oxycodone hydrochloride, hydrocodone bitartrate, and hydromorphone hydrochloride.

In at least one embodiment, the at least one active agent comprises an opioid agonist such as oxycodone or pharmaceutically acceptable salt thereof present in an amount of, for example, about 2.5 mg, 5 mg, 7.5 mg, 10 mg, 15 mg, 20 mg, 25 mg, or 30 mg. In at least one embodiment, the at least one active agent comprises hydrocodone bitartrate present in an amount of, for example, 2.5 mg, 5 mg, 7.5 mg, 10 mg and 15 mg.

In at least one embodiment, the at least one active agent is oxycodone hydrochloride, and the oxycodone hydrochloride has a 14-hydroxycodeinone level of less than about 25 ppm, less than about 15 ppm, less than 5 about 10 ppm, less than about 5 ppm, less than about 2 ppm, less than about 1 ppm, less than about 0.5 ppm or less than about 0.25 ppm. WO 2005/097801 A1, U.S. Pat. No. 7,129,248 B2 and US 2006/0173029 A1, all of which are hereby incorporated by reference, describe a process for preparing oxycodone hydrochloride having low levels of 14-hydroxycodeinone.

In at least one embodiment, the drug susceptible to abuse may be chosen from dronabinol, derivatives thereof and mixtures thereof. As a non-limiting example, the pharmaceutical compositions disclosed herein can comprise natural and synthetic delta-9-tetrahydrocannabinol or any salt, isomer, enantiomer, ester, prodrug, and/or derivative thereof.

In at least one embodiment, the drug susceptible to abuse may be chosen from at least one central nervous system (CNS) stimulant. Non-limiting examples of CNS stimulants include amphetamines, phenidates, CNS depressants, tranquilizers, sedative hypnotics, benzodiazepines, barbiturates, pharmaceutically acceptable salts thereof, and combinations thereof. In at least one embodiment, the at least one active agent may comprise a CNS stimulant or a pharmaceutically acceptable salt, hydrate, or solvate thereof or a mixture thereof. In at least one embodiment, the CNS stimulant comprises at least one amphetamine chosen, for example, from gamma-hydroxybutyrate, dextroamphetamine, dextroamphetamine resin complex, methamphetamine, methylphenidate, sibutramine, methylenedioxymethamphetamine, and pharmaceutically acceptable salts, hydrates, and solvates and mixtures thereof.

In at least one embodiment, the CNS stimulant comprises mixed amphetamines and pharmaceutically acceptable salts, hydrates, and solvates, and mixtures thereof. The mixed amphetamines may include at least one of dextroamphetamine saccharate, amphetamine aspartate, dextroamphetamine sulfate and amphetamine sulfate, and pharmaceutically acceptable salts, hydrates, and solvates and mixtures thereof. In at least one embodiment, the mixed amphetamine includes pharmaceutically acceptable salts of dextroamphetamine saccharate, amphetamine aspartate, dextroamphetamine sulfate, and amphetamine sulfate.

In at least one embodiment, the CNS stimulant comprises a phenidate, such as, for example, methylphenidate or dexmethylphenidate, and pharmaceutically acceptable salts, hydrates, and solvates and mixtures thereof.

Non-limiting examples of benzodiazepines useful as active agents in the pharmaceutical compositions disclosed herein include alprazolam, bromazepam, chlordiazepoxide, clorazepate, diazepam, estazolam, flurazepam, halazepam, ketazolam, lorazepam, nitrazepam, oxazepam, prazepam, quazepam, temazepam, triazolam, and pharmaceutically acceptable salts, hydrates, and solvates and mixtures thereof.

Non-limiting examples of barbiturates useful as active agents in the pharmaceutical compositions disclosed herein include amobarbital, aprobarbotal, butabarbital, butalbital, methohexital, mephobarbital, metharbital, pentobarbital, phenobarbital, secobarbital and pharmaceutically acceptable salts, hydrates, and solvates mixtures thereof.

In at least one embodiment, the pharmaceutical compositions disclosed herein comprise a second active agent, such as a non-opioid analgesic. Non-limiting examples of non-opioid analgesics include acetaminophen and non-steroidal anti-inflammatory agents including, but not limited to, aspirin, celecoxib, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, pharmaceutically acceptable salts, hydrates and solvates thereof and mixtures thereof. In at least one embodiment, the second active agent comprises acetaminophen in the form of granules. A non-limiting example of acetaminophen granules suitable for use in the pharmaceutical compositions disclosed herein are those marketed under trade name COMPRESSO PAP 90 CPF by Granules India.

Alternatively, the second active agent can be an antagonist to the active agent, such as, for example, naltrexone, naloxone, nalmefene, cyclazacine, levallorphan, buprenorphine, pharmaceutically acceptable salts, hydrates and solvates thereof, and mixtures thereof. In at least one embodiment, the antagonist can be an opioid antagonist, non-limiting examples of which include amiphenazole, naltrexone, methylnaltrexone, naloxone, nalbuphine, nalorphine, nalorphine dinicotinate, nalmefene, nadide, levallorphan, cyclozocine, pharmaceutically acceptable salts, hydrates and solvates thereof and mixtures thereof. In at least one embodiment, the antagonist may be combined with the at least one active agent and the ion exchange material such that the antagonist forms a complex with the ion exchange material, in addition to the complex of the at least one active agent and the ion exchange material.

In pharmaceutical compositions having (1) at least one active agent admixed or complexed with the ion exchange material and (2) a second active agent (such as, for example, pharmaceutical compositions in which the admixture or complex containing the at least one active agent is mixed with or coated on a substrate comprising the second active agent), the first active agent can be an opioid agonist and the second active agent can be a non-opioid analgesic. In at least one such embodiment, the non-opioid analgesic is chosen from, for example, acetaminophen and nonsteroidal anti-inflammatory agents (e.g., acetaminophen, ibuprofen, aspirin or diclofenac as described herein) and the opioid agonist is chosen from, for example, oxycodone, hydrocodone or pharmaceutically acceptable salts, hydrates or solvates thereof (such as oxycodone hydrochloride or hydrocodone bitartrate).

In at least one embodiment, the pharmaceutical compositions disclosed herein comprise, for example, from about 2.5 mg to about 10 mg oxycodone or a pharmaceutically acceptable salt thereof; from about 2.5 mg to about 15 mg hydrocodone or a pharmaceutically acceptable salt thereof; from about 300 mg to about 650 mg acetaminophen; from about 50 mg to about 800 mg ibuprofen; and/or from about 325 mg to about 750 mg aspirin.

In at least one embodiment, the pharmaceutical compositions disclosed herein comprise about 2.5 mg oxycodone or a pharmaceutically acceptable salt thereof and about 325 mg acetaminophen; about 5 mg oxycodone or a pharmaceutically acceptable salt thereof and about 325 mg acetaminophen; about 7.5 mg oxycodone or a pharmaceutically acceptable salt thereof and about 325 mg acetaminophen; about 10 mg oxycodone or a pharmaceutically acceptable salt thereof and about 325 mg acetaminophen; about 7.5 mg oxycodone or a pharmaceutically acceptable salt thereof and about 500 mg acetaminophen; about 10 mg oxycodone or a pharmaceutically acceptable salt thereof and about 650 mg acetaminophen; about 5 mg oxycodone or a pharmaceutically acceptable salt thereof and about 500 mg acetaminophen; about 2.5 mg oxycodone or a pharmaceutically acceptable salt thereof and about 300 mg acetaminophen; about 5 mg oxycodone or a pharmaceutically acceptable salt thereof and about 300 mg acetaminophen; about 7.5 mg oxycodone or a pharmaceutically acceptable salt thereof and about 300 mg acetaminophen; about 10 mg oxycodone or a pharmaceutically acceptable salt thereof and about 400 mg acetaminophen; about 2.5 mg oxycodone or a pharmaceutically acceptable salt thereof and about 400 mg acetaminophen; about 5 mg oxycodone or a pharmaceutically acceptable salt thereof and about 400 mg acetaminophen; or about 7.5 mg oxycodone or a pharmaceutically acceptable salt thereof and about 400 mg acetaminophen.

Other non-limiting, exemplary formulations may comprise about 2.5 mg oxycodone or a pharmaceutically acceptable salt thereof and about 325 mg aspirin; about 5 mg oxycodone or a pharmaceutically acceptable salt thereof and about 325 mg aspirin; about 7.5 mg oxycodone or a pharmaceutically acceptable salt thereof and about 325 mg aspirin; about 10 mg oxycodone or a pharmaceutically acceptable salt thereof and about 325 mg aspirin; about 2.5 mg oxycodone or a pharmaceutically acceptable salt thereof and about 500 mg aspirin; about 5 mg oxycodone or a pharmaceutically acceptable salt thereof and about 500 mg aspirin; about 7.5 mg oxycodone or a pharmaceutically acceptable salt thereof and about 500 mg aspirin; about 10 mg oxycodone or a pharmaceutically acceptable salt thereof and about 500 mg aspirin. In certain embodiments, the formulation comprises about 4.8355 mg oxycodone or a pharmaceutically acceptable salt thereof and about 325 mg aspirin.

Further non-limiting, exemplary formulations may comprise about 5 mg hydrocodone or a pharmaceutically acceptable salt thereof and about 500 mg acetaminophen; about 10 mg hydrocodone or a pharmaceutically acceptable salt thereof and about 650 mg acetaminophen; about 7.5 mg hydrocodone or a pharmaceutically acceptable salt thereof and about 750 mg acetaminophen; about 5 mg hydrocodone or a pharmaceutically acceptable salt thereof and about 325 mg acetaminophen; about 7.5 mg hydrocodone or a pharmaceutically acceptable salt thereof and about 325 mg acetaminophen; about 10 mg hydrocodone or a pharmaceutically acceptable salt thereof and about 325 mg acetaminophen; about 7.5 mg hydrocodone or a pharmaceutically acceptable salt thereof and about 650 mg acetaminophen; about 10 mg hydrocodone or a pharmaceutically acceptable salt thereof and about 750 mg acetaminophen; about 10 mg hydrocodone or a pharmaceutically acceptable salt thereof and about 500 mg acetaminophen; about 5 mg hydrocodone or a pharmaceutically acceptable salt thereof and about 400 mg acetaminophen; about 7.5 mg hydrocodone or a pharmaceutically acceptable salt thereof and about 400 mg acetaminophen; about 10 mg hydrocodone or a pharmaceutically acceptable salt thereof and about 400 mg acetaminophen.

Additional non-limiting, exemplary formulations may comprise about 2.5 mg hydrocodone or a pharmaceutically acceptable salt thereof and about 200 mg ibuprofen; about 5 mg hydrocodone or a pharmaceutically acceptable salt thereof and about 200 mg ibuprofen; about 7.5 mg hydrocodone or a pharmaceutically acceptable salt thereof and about 200 mg ibuprofen; or about 10 mg hydrocodone or a pharmaceutically acceptable salt thereof and about 200 mg ibuprofen.

Excipients

The pharmaceutical composition according to the disclosure can further comprise one or more pharmaceutically acceptable excipients. Such pharmaceutically acceptable excipients may be chosen, for example, from inert diluents such as lactose; granulating and disintegrating agents such as cornstarch; binding agents such as starch; bulking agents such as microcrystalline cellulose; glidants such as colloidal silicon dioxide; and lubricating agents such as magnesium stearate, among other excipients known to those of ordinary skill in the art.

Examples of possible pharmaceutically acceptable excipients are described in the Handbook of Pharmaceutical Excipients, American Pharmaceutical Association (2012), which is incorporated by reference herein. Suitable excipients include, but are not limited to, plasticizers, colorants, lubricants, thermal lubricants, antioxidants, buffering agents, disintegrants or granulating agents, binding agents, diluents, glidants, anti-adherants, sweeteners, chelating agents, granulating agents, bulking agents, flavorants, surfactants, solubilizers, stabilizers, hydrophilic polymers, hydrophobic polymers, waxes, lipophilic materials, absorption enhancers, preservative, absorbent, cross-linking agents, bioadhesive polymers, pore formers, osmotic agents, polycarboxylic acids, and combinations thereof.

Examples of suitable binding agents include, but are not limited to, cellulosic polymers (e.g., hydroxypropylmethylcellulose, hydroxypropylcellulose, hydroxyethylcellulose, etc.), polyethylene glycol, an acrylic polymer, an acrylic copolymer, a graft copolymer of polyvinyl alcohol and polyethylene glycol, a polyvinyl alcohol, alginic acid, sodium alginate, starch, pregelatinized starch, sucrose, guar gum, salts thereof, derivatives thereof and combinations thereof. Additional binders include, but are not limited to, natural or synthetic waxes, fatty alcohols (e.g., lauryl, myristyl, stearyl, cetyl or cetostearyl alcohol), fatty acids, including, but not limited to, fatty acid esters, fatty acid glycerides (e.g., mono-, di-, and tri-glycerides), hydrogenated fats, hydrocarbons, stearic acid, hydrophobic and hydrophilic materials having hydrocarbon backbones, acacia, tragacanth, sucrose, gelatin, glucose, cellulose materials (e.g., methylcellulose and sodium carboxymethylcellulose (e.g., Tylose™)), magnesium aluminum silicate, polysaccharide acids, bentonites, polyvinylpyrrolidone (povidone), polymethacrylates, and pregelatinized starch (such as National™ 1511 and Starch 1500). Suitable waxes include, for example, beeswax, glycowax, castor wax, carnauba wax and other wax-like substances. A "wax-like" substance is defined as any material which is normally solid at room temperature and has a melting point of from about 30° C. to about 100° C.

Additional examples of binders which may be used include, but are not limited to, digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils, natural and synthetic waxes and polyalkylene glycols. In certain embodiments, hydrocarbons having a melting point of between 25° C. and 90° C. may be included. Of the long-chain hydrocarbon binder materials, fatty (aliphatic) alcohols can be incorporated into the mixture according to certain embodiments. In further embodiments, the mixture or pharmaceutical composition may contain up to 80% (by weight) of at least one digestible, long chain hydrocarbon.

Examples of suitable disintegrants include, but are not limited to, sodium starch glycolate, clays (such as Veegum™ HV), celluloses (such as purified cellulose, methylcellulose, sodium carboxymethylcellulose, and carboxymethylcellulose), cross-linked sodium carboxymethylcellulose, starch, cross-linked polyvinylpyrrolidone (e.g., crospovidone), alginates, cornstarches and pre-gelatinized corn starches (such as National™ 1551 and National™ 1550), gums (such as agar, guar, locust bean, pectin, and tragacanth) and mixtures thereof. Disintegrants can be added at any suitable step during the preparation of the pharmaceutical compositions, such as prior to granulation or during a lubrication step prior to compression or encapsulation. The pharmaceutical compositions as described herein can include one or more disintegrants in the range of about 0.5% to about 30%, or about 1% to about 10%, or about 2% to about 6%, of the total weight of the formulation.

Suitable bulking agents include, but are not limited to, starches (e.g., corn starch), microcrystalline cellulose, lactose (e.g., lactose monohydrate), sucrose, dextrose, mannitol, calcium phosphate and dicalcium phosphate.

According to certain embodiments, the pharmaceutical compositions may include a plasticizer. Plasticizers may interact with hydrophobic materials resulting in a lower viscosity of the mixture as compared to the mixture without the plasticizer when measured under the same conditions. Certain plasticizers may lower the glass transition temperature (Tg) of hydrophobic materials. Suitable plasticizers include, but are not limited to, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers may include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutyl sebacate, acetyltributylcitrate, triethyl citrate, acetyl triethyl citrate, tributyl citrate and allyl glycolate. In certain embodiments, the plasticizer may be in an amount of about 5% or less, or about 4% or less, or about 2% or less, or 0% (i.e., plasticizer free).

In at least one embodiment, the pharmaceutical composition includes a glidant. A glidant is an excipient that improves the flow characteristics of a compressible powder such as tablet ingredients or granules. Suitable glidants include, but are not limited to, silicon dioxide, colloidal silicon dioxide and the like.

Suitable diluents useful in pharmaceutical compositions as described herein include, but are not limited to, lactose (e.g., lactose (anhydrous), lactose (spray dried), lactose monohydrate), starch (e.g., directly compressible starch), mannitol, sorbitol, dextrose monohydrate, microcrystalline cellulose, dibasic calcium phosphate dihydrate, sucrose-based diluents, confectioner's sugar, monobasic calcium sulfate monohydrate, calcium sulfate dihydrate, calcium lactate trihydrate granular, dextrates (e.g., Emdex™), dextrose (e.g., Cerelose™), inositol, hydrolyzed cereal solids such as the Maltrons™ and Mor-Rex™ amylose, powdered cellulose (e.g., Elcema™), calcium carbonate, glycine, bentonite, polyvinylpyrrolidone, and the like. In certain embodiments, the pharmaceutical compositions described herein can include the diluents in the range of about 5% to about 99%, or from about 25% to about 90%, or from about 40% to about 80%, of the total weight of the formulation. Lactose has a melting point of about 202° C. Microcrystalline cellulose has a burning point of over 200° C. before it reaches a melting point, and therefore is also suitable as it does not have a low melting point.

Suitable lubricants include, but are not limited to, glyceryl behenate (Compritol™ 888), metallic stearates (e.g., magnesium, calcium and sodium stearates), stearic acid, hydrogenated vegetable oils (e.g., Sterotex™), talc, waxes such as beeswax and carnauba wax, silica, fumed silica, colloidal silica, calcium stearate, long chain fatty alcohols, boric acid, sodium benzoate and sodium acetate, sodium chloride, DL-Leucine, polyethylene glycols (e.g., Carbowax™ 4000 and Carbowax™ 6000), sodium oleate, sodium benzoate, sodium acetate, sodium lauryl sulfate, sodium stearyl fumarate (Pruv™), magnesium lauryl sulfate, stearic acid, stearyl alcohol, mineral oil, paraffin, micro crystalline cellulose, glycerin, propylene glycol and combinations thereof. In certain embodiments, the pharmaceutical compositions may include one or more lubricants in an amount of from about 0.1% to about 10%, or from about 0.2% to about 8%, or from about 0.25% to about 5%, of the total weight of the formulation. Magnesium stearate is a lubricant suitable for use in certain embodiments of the pharmaceutical compositions. Magnesium stearate has a melting point of about 90° C. Although magnesium stearate has a low melting point, it can be utilized in small amounts (e.g., about 0.5%) as a lubricant without significantly affecting the stability of the peripheral opioid formulations of the present invention.

Suitable anti-adherents include, but are not limited to, talc, cornstarch, colloidal silicone dioxide (Cab-O-Sil™), DL-Leucine, sodium lauryl sulfate, and metallic stearates. In certain embodiments, the pharmaceutical compositions can include an anti-adherent in an amount from about 0.1% to about 15%, or from about 0.25% to about 10%, or from about 0.5% to about 5%, of the total weight of the formulation. Colloidal silicon dioxide is an anti-adherent agent suitable for use in some embodiments of the pharmaceutical compositions in an amount from about 0.1% to about 10%, or from about 0.25% to about 5%, or from about 0.5% to about 2%, of the total weight of the formulation. Colloidal silicon dioxide has a melting point of about 1700° C.

Other excipients (such as colorants, flavors and sweeteners) can be utilized in embodiments of the pharmaceutical compositions where they impart little to no deleterious effect on the stability of the pharmaceutical composition.

In certain embodiments, the pharmaceutical composition may include a film coat. The film coat may include, but is not limited to, hydroxypropylmethylcellulose, polyethylene glycol, polyvinyl alcohol or a mixture of any two or more thereof. According to certain embodiments, the film coat may provide a weight gain to the tablet of about 5% or less, or about 4% or less, or about 2% or less.

In certain embodiments, the pharmaceutical composition can further comprise additional materials for deterring abuse such as gelling agents, bittering agents, and/or irritants. As non-limiting examples, the gelling agent may be chosen from sugars, sugar derived alcohols, starch, starch derivatives such as pregelatinized starch, cellulose derivatives, attapulgites, bentonites, dextrins, alginates, carrageenan, gums, pectins, gelatin, kaolin, lecithin, magnesium aluminum silicate, carbomers, carbopols, polyvinylpyrrolidone, polyethylene glycol, polyethylene oxide, polyvinyl alcohol, silicon dioxide, curdlan, furcelleran, egg white powder, lacto albumin, soy protein, chitosan, surfactants such as but not limited to sodium laurel sulfate, emulsifiers, and pharmaceutically acceptable salts thereof and mixtures thereof. A non-limiting example of a pregelatinized starch suitable for use in the pharmaceutical compositions disclosed herein is the product sold under trade name SWELSTAR MX-1 by Asahi Kasei. A non-limiting example of a gum suitable for use in the pharmaceutical compositions disclosed herein is xanthan gum, such as, for instance, the product sold under trade name XANTURAL 180 by CP Kelco. As non-limiting examples, the bittering agent may be chosen from flavor oils, flavoring aromatics, oleoresins, plant extracts, leaf extracts, flower extracts, fruit extracts, sucrose derivatives, chlorosucrose derivatives, quinine sulphate, denatonium benzoate, and mixtures thereof. As non-limiting examples, the irritant may be chosen from surfactants, capsaicin, capsaicin analogs, and mixtures thereof.

Dosage Forms

The pharmaceutical compositions disclosed herein can be in solid oral dosage form such as a pharmaceutically acceptable tablet or capsule. Typically, mixtures or blends of dried particles or granules containing, for example, (1) the admixture or complex of the at least one active agent and the ion exchange material and (2) optionally, excipients, are compressed into tablets or encapsulated in pharmaceutically acceptable capsules. Alternatively, the mixtures or blends of dried particles or granules may comprise (1) a coating of the admixture or complex upon (2) a substrate, which may or may not comprise the same or a different active agent as the admixture or complex, and (3) optionally, excipients, which may then be compressed into tablets or encapsulated in pharmaceutically acceptable capsules.

The pharmaceutical compositions disclosed herein may comprise immediate release dosage forms prepared using any suitable method known in the art.

Methods of Making

The present disclosure also provides methods of preparing the pharmaceutical composition disclosed herein, comprising (i) combining a least one active agent and an ion exchange material to form an admixture or complex of the at least one active agent and the ion exchange material, and (ii) incorporating the admixture or complex into a pharmaceutical composition, wherein the composition releases about 75% or more of the at least one active agent within about 1 hour as measured by in-vitro dissolution in a USP Apparatus 2 (paddle) at about 50 rpm in about 900 ml 0.1N HCl at about 37° C.

Figure 2:
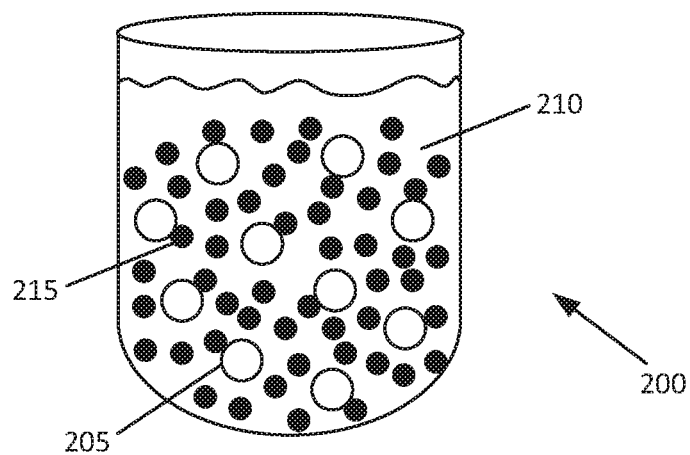
FIG. 2 is a graphical depiction of a pharmaceutical composition comprising a complex of at least one active agent and an ion exchange material, formed in the presence of an aqueous medium, according to an exemplary embodiment of the present disclosure.

Referring to FIGS. 1 and 2, according to various example embodiments, the present disclosure provides pharmaceutical compositions such as tablets and capsules wherein (a) an admixture 100 of at least one active agent 105 and ion exchange resin 110 is formed in the absence of an aqueous medium or (b) a complex 200 of at least one active agent 205 and ion exchange resin 215 is formed in the presence of an aqueous medium 210.

As such, in at least one embodiment, the methods of preparing the pharmaceutical compositions disclosed herein comprise (i) preparing an aqueous mixture by combining the at least one active agent, the ion exchange material, and an aqueous medium; and (ii) drying the aqueous mixture. The at least one active agent, the ion exchange material, and the aqueous medium can be combined in any order. In certain embodiments, however, preparing the aqueous mixture comprises (i) preparing a solution of the active agent in the aqueous medium and (ii) adding the ion exchange material to the solution.

In at least one embodiment, the at least one active agent is added to the aqueous medium in an amount such that the they form a solution having a concentration of the at least one active agent in the aqueous medium ranging from, as non-limiting examples, about 10 mg/mL to about 100 mg/mL, from about 20 mg/mL to about 90 mg/mL, from about 30 mg/mL to about 80 mg/mL, from about 40 mg/mL to about 70 mg/mL, or from about 50 mg/mL to about 60 mg/mL (step 305). In at least one embodiment, the concentration of the at least one active agent in the aqueous medium is about 50 mg/mL.

In at least one embodiment, the ion exchange material is added to the at least one active agent in an amount such that the weight ratio of the ion exchange material to the at least one active agent in the mixture (with or without an aqueous medium) ranges, as non-limiting examples, from about 1:1 to about 20:1, or about 1:1 to about 10:1 such as from about 4:1 to about 6:1, or such as from about 3:1 to about 5:1. In at least one embodiment, the ion exchange material and the at least one active agent are combined at a weight ratio chosen from about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, and about 20:1. In at least one embodiment, the weight ratio of ion exchange material to the at least one active agent is about 5:1 when the ion exchange material and the at least one active agent are mixed.

In at least one embodiment, the method comprises letting the aqueous mixture of the at least one active agent, the ion exchange material, and an aqueous medium stand for a period of about 24 hours or less, about 12 hours or less, about 8 hours or less, about 4 hours or less, about 2 hours or less, about 1.5 hours or less, about 1 hour or less, about 50 minutes or less, about 45 minutes or less, about 40 minutes or less, about 30 minutes or less, about 20 minutes or less, about 15 minutes or less, about 10 minutes or less, or about 5 minutes or less. In at least one embodiment, the standing aqueous mixture is agitated, e.g., by stirring or shaking, for at least a portion of the time, and, in at least some embodiments, all of the time, prior to drying. Accordingly, in at least one embodiment, the aqueous mixture is left to stand, while mixing, for about 2 hours. In at least one embodiment, however, it is not necessary to let the aqueous mixture stand prior to drying.

In at least one embodiment, after combining the at least one active agent, the ion exchange material, and the aqueous medium, the resulting aqueous mixture is dried, as non-limiting examples, via spray drying, top drying, or forced air drying such as in a fluid bed dryer or an oven, or any other suitable drying method known in the art for a period of time ranging, for example, from about 15 minutes to about 12 hours, from about 1 hour to about 4 hours, or from about 1 hour to about 2 hours. In at least one embodiment, the resulting aqueous mixture is dried in a fluid bed dryer for about 1 hour.

One or more substrates can be incorporated. In at least one non-limiting example, the substrate comprises sugar spheres or particles, and the complex of the at least one active agent and the ion exchange material is mixed with the sugar spheres or particles, thereby forming a complex-substrate granulation or a complex-substrate composition. In at least one other embodiment, the substrate may comprise a second active agent, such as, for example, acetaminophen in granular form, such that the mixing results in a complex-substrate granulation or composition comprising at least two active agents.

In at least one embodiment, the complex-substrate granulation or composition is incorporated into the pharmaceutical composition without washing or rinsing. However, washing and rinsing is not excluded from the scope of the disclosure.

Figure 3:
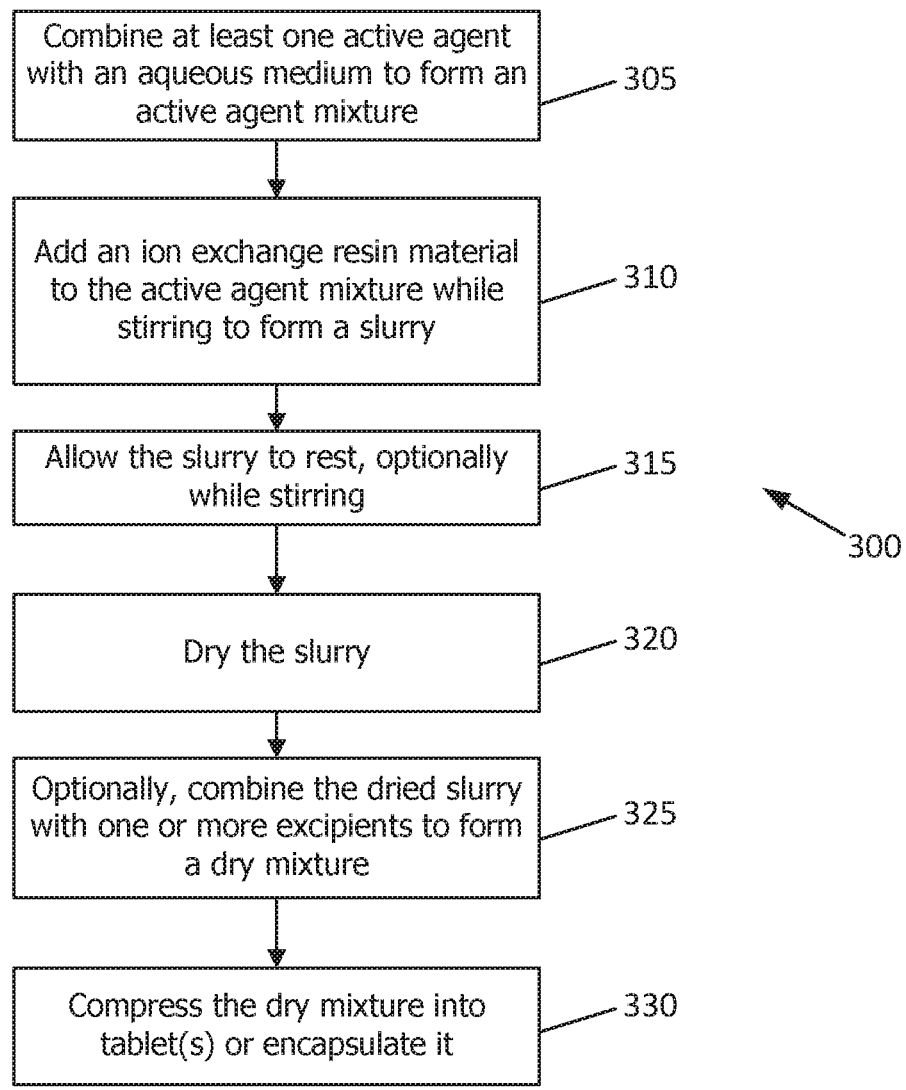
FIG. 3 is a flow chart of an exemplary method for preparing a pharmaceutical composition comprising a complex of at least one active agent and an ion exchange material, according to an exemplary embodiment of the present disclosure.

FIG. 3 is a flow chart of an exemplary method 300 for preparing a pharmaceutical composition comprising a complex of an active agent and an ion exchange material, according to an exemplary embodiment of the present disclosure. As shown in FIG. 3, method 300 may include combining at least one active agent (such as, for example, oxycodone hydrochloride) and an aqueous medium (such as, for example, water) to form a mixture (step 305) having, for example, a concentration of the at least one active agent in the aqueous medium of about 10 mg/mL to about 100 mg/mL, or about 50 mg/mL. Method 300 may also include adding an ion exchange material (such as, for example, AMBERLITE® IRP69) to the mixture while stirring to form a slurry or suspension (step 310). Method 300 may further include letting the slurry or suspension stand, with or without mixing, for a period of time ranging, for example, from about 5 minutes to about 24 hours, such as about 2 hours (step 315). Method 300 may further include drying the slurry or suspension in, for example, a fluid bed dryer for a period of time ranging, for example, from about 15 minutes to about 12 hours, such as, about 2 hours (step 320). Optionally, method 300 may include mixing the dried slurry or suspension with at least one excipient (step 325) and compressing the resulting dry mixture into tablets or encapsulating the resulting dry mixture in capsules (step 330).

Figure 4:
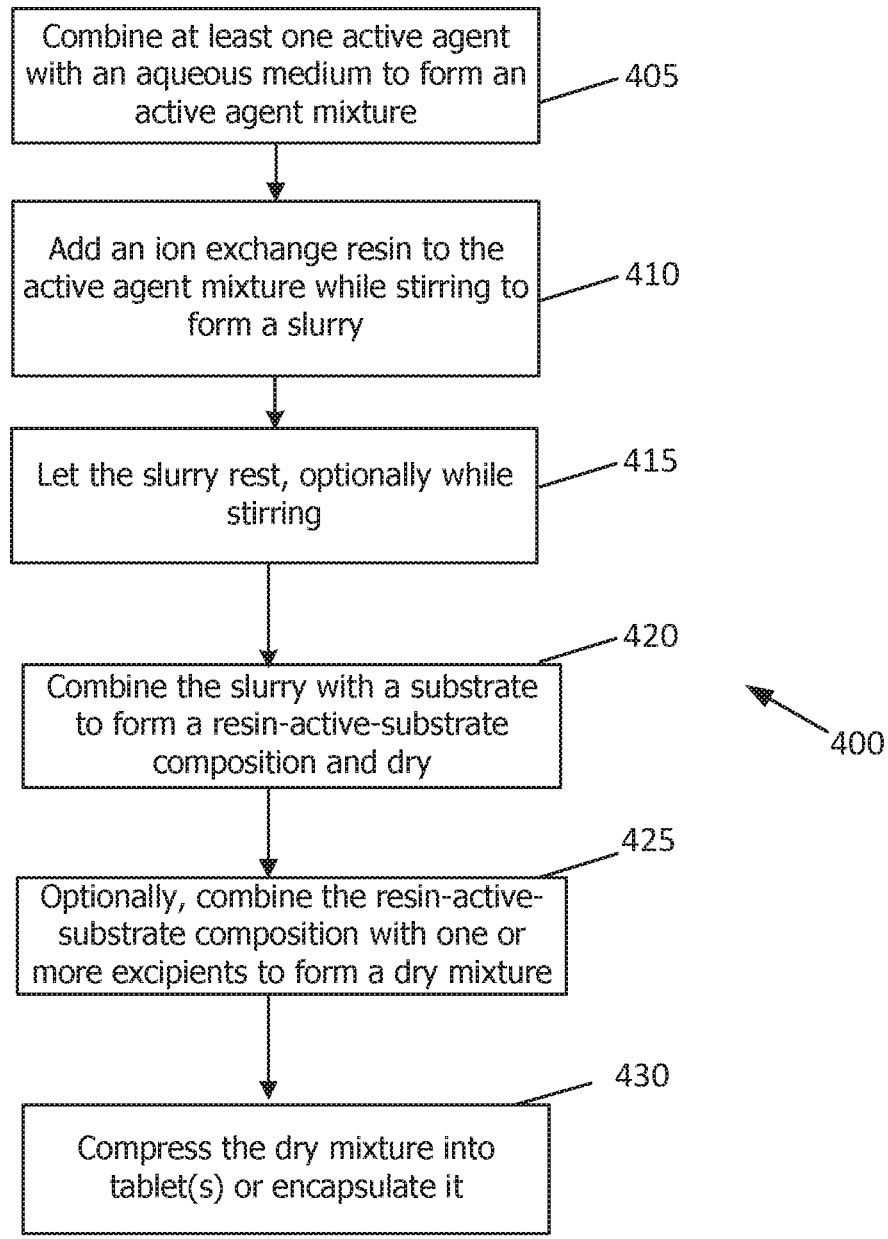
FIG. 4 is a flow chart of an exemplary method for preparing a pharmaceutical composition comprising a complex of at least one active agent and an ion exchange material, according to an exemplary embodiment of the present disclosure.

FIG. 4 is a flow chart of an exemplary method 400 for preparing a pharmaceutical composition comprising a complex of at least one active agent and an ion exchange material, according to an exemplary embodiment of the present disclosure. As shown in FIG. 4, method 400 may include combining at least one active agent (such as, for example, oxycodone hydrochloride) and an aqueous medium (such as, for example, water) to form a mixture (step 405) having, for example, a concentration of the at least one active agent in the aqueous medium of about 10 mg/mL to about 100 mg/mL, or about 50 mg/mL. Method 400 may also include adding an ion exchange material (such as, for example, AMBERLITE® IRP69) to the mixture while stirring to form a slurry or suspension (step 410). Method 400 may optionally further include letting the slurry or suspension stand, with or without mixing, for a period of time ranging, for example, from about 5 minutes to about 24 hours, such as about 2 hours (step 415). Method 400 may further include combining the slurry or suspension with a substrate (such as, for example, particles or granules of a second active agent, sugar spheres, or any other suitable substrate known in the art) and drying (step 420). In at least one embodiment, step 420 may comprise combining the slurry or the suspension and the substrate by spray drying or top spraying the slurry or suspension onto the substrate using a fluid bed dryer for an amount of time suitable to form a dry complex-substrate granulation or composition, wherein the amount of time suitable may range, for example, from about 15 minutes to about 12 hours, from about 1 hour to about 4 hours, or from about 1 hour to about 2 hours. In at least one embodiment of step 420, the slurry or suspension is mixed with the substrate and dried in a fluid bed dryer for about 1 hour to form a complex-substrate composition. Method 400 may optionally include adding at least one excipient to the complex-substrate composition (step 425) and compressing the resulting mixture into tablets or encapsulating the resulting mixture in capsules (step 430).

In at least one embodiment, the methods of preparing the pharmaceutical compositions disclosed herein comprise combining the at least one active agent and ion exchange material to form an admixture. In such at least one embodiment, the method comprises mixing the at least one active agent with the ion exchange material in the absence of an aqueous medium and forming a pharmaceutical composition by, as non-limiting examples, granulating the resulting dry mixture to form granules and either compressing the granules into tablets or filling capsules with the granules using any suitable technique known in the art. In at least one optional embodiment, the admixture of the at least one active agent and ion exchange material may be combined with (1) a substrate comprising an active agent which is the same as or different than the at least one active agent and (2) optional excipients as disclosed herein to form a dry mixture which may be granulated prior to compression into tablets or encapsulation in capsules using any suitable technique known in the art.

Methods of Using

The present disclosure relates to methods of treating pain comprising administering to a patient in need thereof a pharmaceutical composition disclosed herein, such as, for example, a pharmaceutical composition comprising an opioid analgesic, or an opioid analgesic together with acetaminophen or other non-steroidal anti-inflammatory agent, wherein the opioid analgesic forms an admixture or a complex with an ion exchange material as described herein.

The present disclosure also relates to methods of treating attention deficit disorder (ADHD) comprising administering to a patient in need thereof a pharmaceutical composition disclosed herein, such as, for example, a pharmaceutical composition comprising an admixture or a complex of a central nervous system stimulant and an ion exchange material as described herein.

The present disclosure further relates to methods of deterring abuse of a drug susceptible to abuse (such as, for example, opioid agonists) comprising preparing a pharmaceutical composition disclosed herein, such as, for example, a pharmaceutical composition comprising an admixture or a complex of an opioid agonist and an ion exchange material as described herein.

The following examples illustrate various embodiments of the present disclosure. They are not intended to be construed to limit the claims in any manner whatsoever.

EXAMPLES

Example 1

Exemplary Method for Making Oxycodone HCl/Acetaminophen Resinate Tablets

Tablet compositions comprising an oxycodone HCl/ion exchange resin complex equivalent to 5 mg oxycodone HCl and 325 mg acetaminophen were prepared according to the following general procedure:
1. Dissolve oxycodone hydrochloride in water to form, for example, a 50 mg/mL oxycodone hydrochloride/water solution.
2. Form a slurry by adding AMBERLITE® IRP69 resin to the oxycodone hydrochloride/water solution, while stirring, in an amount such that the weight ratio of ion exchange resin to active agent in the resulting slurry is about 5:1. Continue stirring the slurry for about 20 hours.
3. Combine the slurry with a substrate (i.e., acetaminophen granules) and dry by top spraying the slurry onto the substrate using a fluid bed dryer for about 2 hours to form a dry complex-substrate granulation or composition comprising acetaminophen particles and oxycodone HCl/resin (i.e., an oxycodone HCl-resin-acetaminophen granulation.)
4. Optionally blend the resulting oxycodone HCl-resin-acetaminophen granulation with one or more excipients to form a blend.
5. Compress the resulting blend to form round tablets comprising 5 mg oxycodone HCl and 325 mg acetaminophen.

Example 2

Oxycodone HCl/Acetaminophen 5 mg/325 mg Resinate Tablet Composition Example The procedure set forth in Example 1 was used to make tablet compositions comprising an oxycodone HCl/ion exchange resin complex equivalent to 5 mg oxycodone HCl and 325 mg acetaminophen and having the following composition, as set forth in TABLE 1:

TABLE 1

| Ingredient | Amount (mg/tablet) | Weight Percentage (%) |
| --- | --- | --- |
| Oxycodone HCl | 5 | 1.05 |
| Amberlite IRP 69 | 25 | 5.27 |
| Acetaminophen granules (90% acetaminophen; 10% excipients) | 361.11 | 76.17 |
| Pregelatinized starch | 4.75 | 1 |
| Xanthan gum | 3.55 | 0.75 |
| Crospovidone | 71.1 | 15 |
| Magnesium stearate | 3.55 | 0.75 |
| Total Tablet Weight | 474 | 100 |

Example 3

Figure 5:
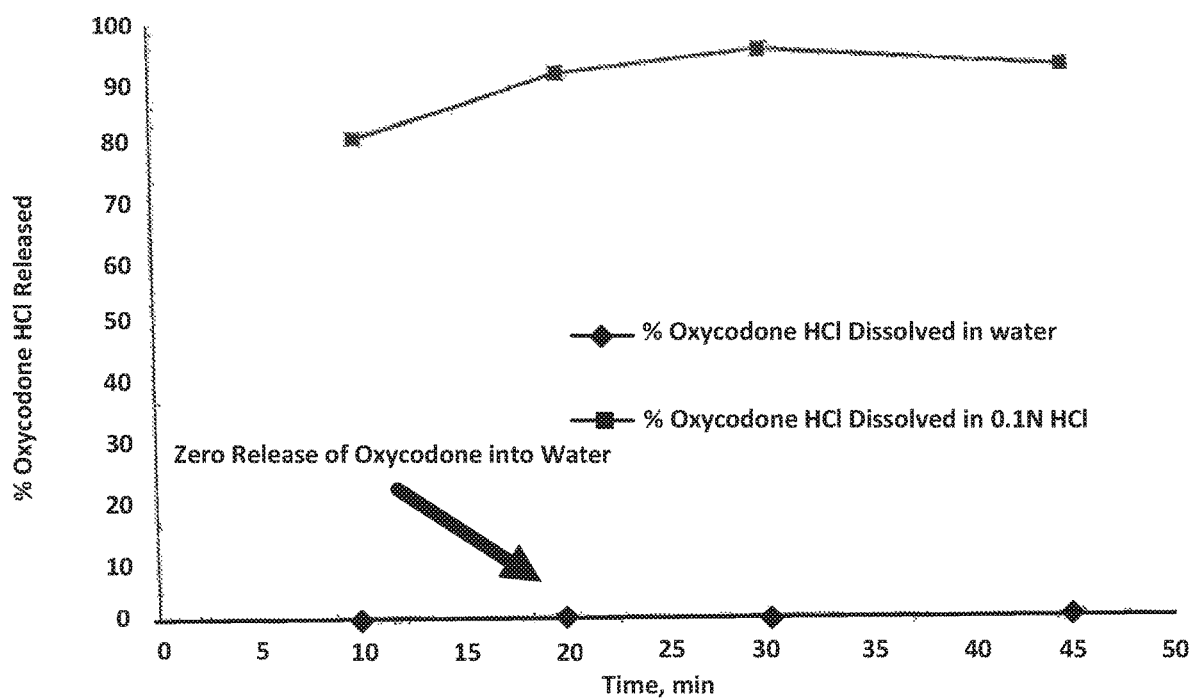
FIG. 5 is a graph presenting oxycodone HCl dissolution data for an exemplary composition comprising oxycodone HCl, ion exchange material, and acetaminophen, according to an exemplary embodiment of the present disclosure.
Figure 6:
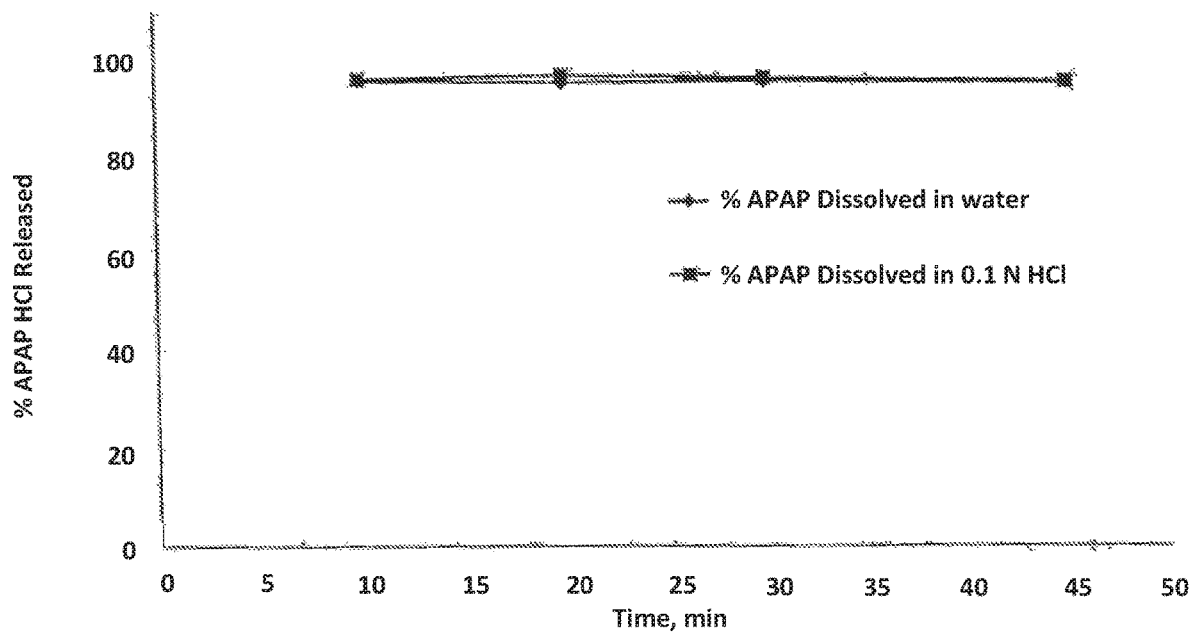
FIG. 6 is a graph presenting acetaminophen dissolution data for an exemplary composition comprising oxycodone HCl, ion exchange material, and acetaminophen, according to an exemplary embodiment of the present disclosure.

Dissolution Profiles of Oxycodone HCl and Acetaminophen from Oxycodone HCl/Acetaminophen 5 mg/325 mg Resinate Granules in Water and 0.1 N HCl An oxycodone HCl-resin-acetaminophen granulation prepared using the procedure set forth in Example 1 up to step 3 was subjected to in-vitro dissolution in either 900 ml water or 900 ml 0.1 N HCl using a USP Apparatus 2 (paddle) at 50 rpm. The results for oxycodone HCl are set forth in FIG. 5. The results for acetaminophen are set forth in FIG. 6.

Example 4

Figure 7:
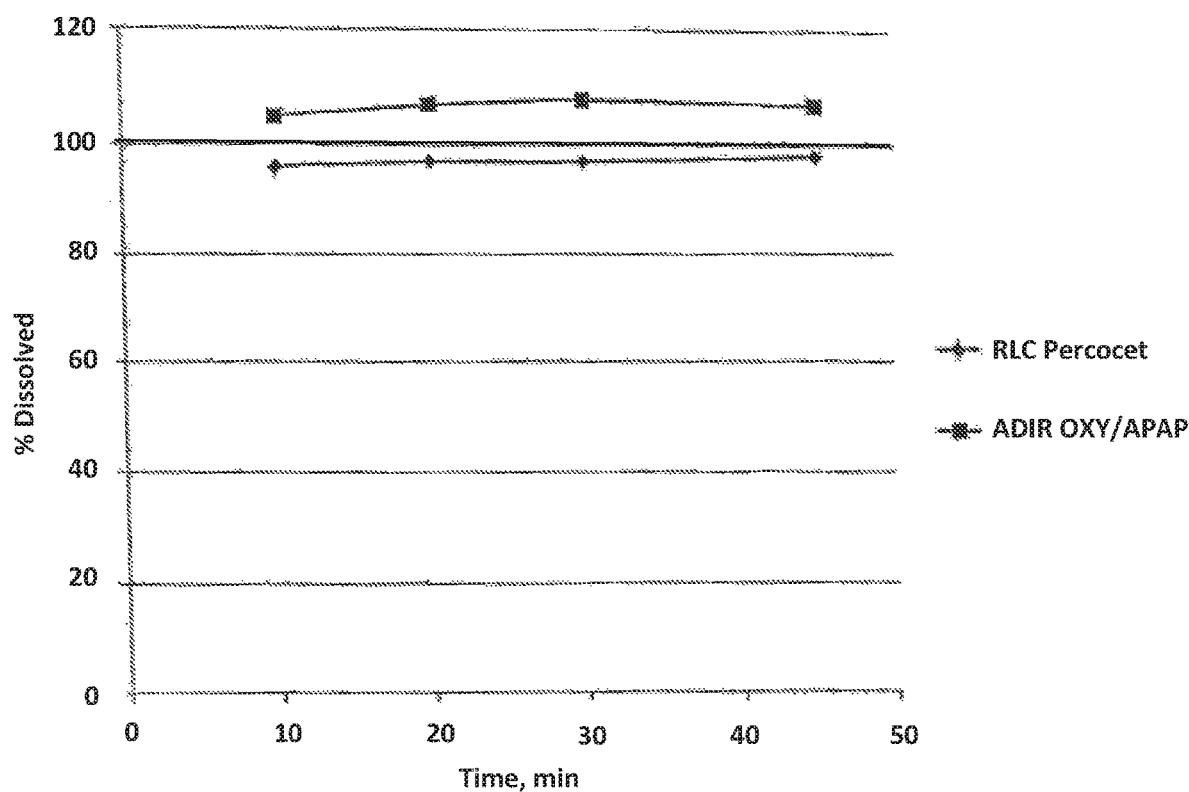
FIG. 7 is a graph presenting acetaminophen dissolution data for an exemplary composition comprising oxycodone HCl, ion exchange material, and acetaminophen as compared to a reference, according to an exemplary embodiment of the present disclosure.
Figure 8:
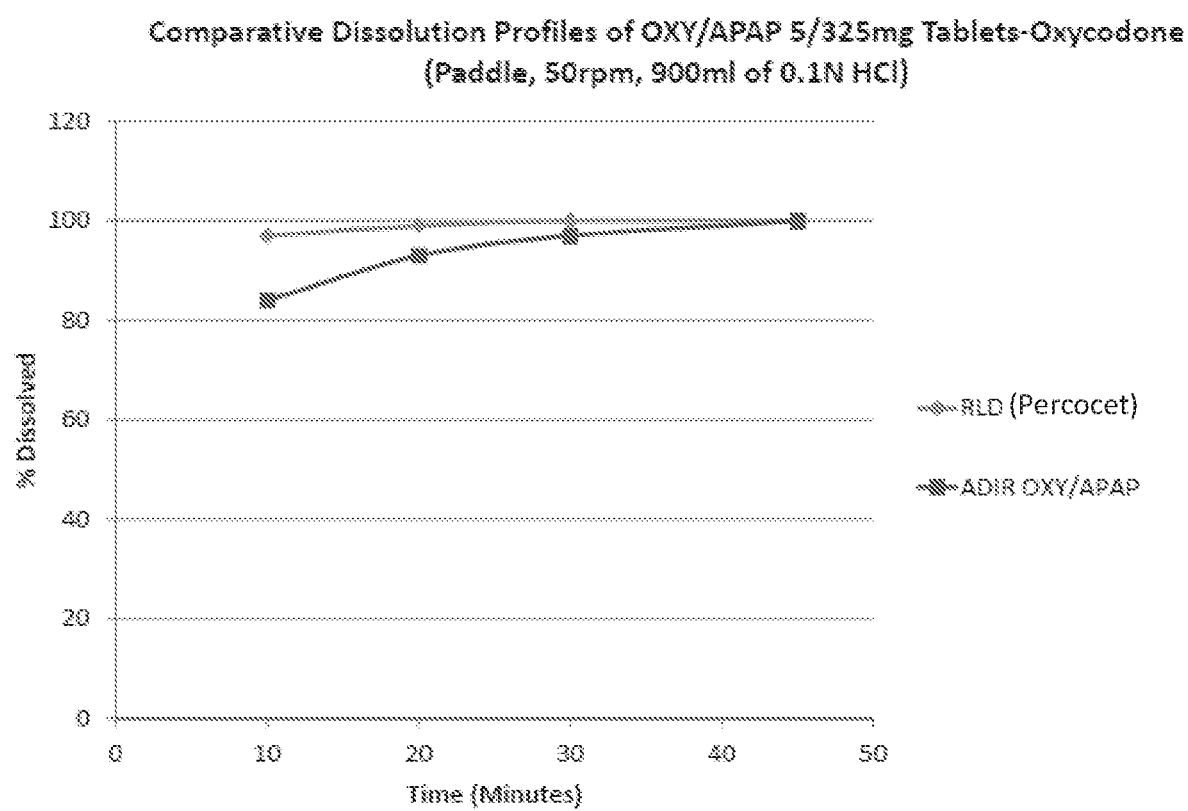
FIG. 8 is a graph presenting oxycodone HCl dissolution data for an exemplary composition comprising oxycodone HCl, ion exchange material, and acetaminophen as compared to a reference, according to an exemplary embodiment of the present disclosure.

Comparative Dissolution Profiles of Oxycodone HCl and Acetaminophen from Oxycodone HCl/Acetaminophen 5 mg/325 mg Resinate Tablets in 0.1 N HCl Relative to a Reference The oxycodone HCl-resin-acetaminophen tablets of Example 2 were subjected to in-vitro dissolution in 900 ml 0.1 N HCl using a USP Apparatus 2 (paddle) at 50 rpm. The results for acetaminophen as compared to a reference (Percocet®) are set forth in FIG. 7. The results for oxycodone HCl as compared to a reference (Percocet®) are set forth in FIG. 8.

Example 5

Syringeability of Oxycodone Hydrochloride from Oxycodone HCl/Acetaminophen 5 mg/325 mg Resinate Tablets in Aqueous Solvents Tablets of Example 2 were tested for syringeability of oxycodone HCl in the solvents tap water, saline, vinegar and 40% ethanol under both boiling and non-boiling conditions. To test for syringeability of oxycodone HCl in the solvent tap water, a tablet was crushed using a mortar and pestle and then placed in a 10 mL container. Five mL of tap water at room temperature were added to the 10 mL container, and the contents mixed. A syringe having a 27-gauge needle was then inserted into the resulting mixture with a cotton ball being used as a filter and the plunger drawn back by hand for a period of time which did not exceed 5 minutes. The contents of the syringe were then measured and analyzed using HPLC.

This procedure was repeated using each of 40% ethanol, saline, and vinegar as the solvent in place of tap water. In addition, for each solvent, the procedure was repeated with the additional step of raising the temperature of the contents of the 10 mL container from room temperature to boiling before inserting the syringe.

The results of the syringeability studies are set forth in TABLE 2. The "Amt. Aspirated" column lists the volume of total mixture content aspirated or extracted into the syringe. The "% Extracted Oxcycodone HCl" column presents the amount of oxycodone HCl present in the syringe relative to the total amount of oxycodone HCl originally in the tablet.

TABLE 2

Syringeability of Oxycodone HCl and Acetaminophen Tablets, 5 mg/325 mg

| Solvent | Trial | Amt. Aspirated (mL) | % Extracted Oxycodone HCl |
|---|---|---|---|
| 40% EtOH | 1 | 0.4 | 1.33 |
|  | 2 | <0.1 | 1.33 |
| 40% EtOH—Boiled | 1 | 0.4 | 2.23 |
|  | 2 | 0.1 | 0.29 |
| Saline | 1 | 0.2 | 1.63 |
|  | 2 | <0.1 | 0.37 |
| Saline—Boiled | 1 | 0.6 | 6.96 |
|  | 2 | N/A/ | N/A |
| Tap water | 1 | 0.2 | 0.34 |
|  | 2 | 0.6 | 2.00 |
| Tap water—Boiled | 1 | 0.2 | 1.17 |
|  | 2 | 0.1 | 0.18 |
| Vinegar | 1 | 0.2 | 0.82 |
|  | 2 | 0.1 | 0.19 |
| Vinegar—Boiled | 1 | 0.6 | 3.71 |
|  | 2 | 0.5 | 3.33 |

Example 6

Oxycodone HCl/Acetaminophen 5 mg/325 mg Resinate Tablet Composition Example

The procedure set forth in Example 1 was used to make tablet compositions comprising an oxycodone HCl/ion exchange resin complex equivalent to 5 mg oxycodone hydrochloride and 325 mg acetaminophen and having the following composition (TABLE 3):

TABLE 3

| Ingredient | Amount (mg/tablet) | Weight Percentage (%) |
|---|---|---|
| Oxycodone HCl-Amberlite IRP 69 resinate-acetaminophen granules | 390.5 | 97.25 |
| Colloidal silicon dioxide | 4.0 | 1 |
| Crospovidone | 4.0 | 1 |
| Magnesium stearate | 3.0 | 0.75 |
| Total Tablet Weight | 401.5 | 100 |

Example 7

Syringeability of Oxycodone HCl from Oxycodone HCl/Acetaminophen 5 mg/325 mg Resinate Tablets in Aqueous Solvents Tablets of Example 6 were tested for syringeability of oxycodone HCl in the solvents tap water, saline, vinegar and 40% ethanol under both boiling and non-boiling conditions using the same procedure for testing syringeability set forth in Example 5. The results are set forth in TABLE 4.

TABLE 4

Syringeability of Oxycodone HCl and Acetaminophen Tablets, 5 mg/325 mg

| Solvent | Trial | Amt. Aspirated (mL) | % Extracted Oxycodone HCl |
|---|---|---|---|
| 40% EtOH | 1 | 1.6 | 5.16 |
|  | 2 | <0.1 | 0.00 |
| 40% EtOH — Boiled | 1 | 1.6 | 9.55 |
|  | 2 | 2.0 | 13.32 |

TABLE 4-continued

Syringeability of Oxycodone HCl and Acetaminophen Tablets, 5 mg/325 mg

| Solvent | Trial | Amt. Aspirated (mL) | % Extracted Oxycodone HCl |
|---|---|---|---|
| Saline | 1 | 0.6 | 3.76 |
|  | 2 | 0.6 | 3.53 |
| Saline — Boiled | 1 | 2.6 | 34.74 |
|  | 2 | 2.5 | 28.69 |
| Tap water | 1 | 2.6 | 3.71 |
|  | 2 | 1.5 | 1.74 |
| Tap water — Boiled | 1 | 2.4 | 8.16 |
|  | 2 | 1.4 | 2.38 |
| Vinegar | 1 | 0.4 | 3.60 |
|  | 2 | 1.4 | 7.77 |
| Vinegar — Boiled | 1 | 1.4 | 1.12 |
|  | 2 | 2.0 | 10.11 |

Example 8

Exemplary Method for Making Hydrocodone Bitartrate/Acetaminophen Resinate Tablets Tablet compositions comprising a hydrocodone/ion exchange resin complex equivalent to 5 mg hydrocodone bitartrate and 300 mg acetaminophen were prepared according to the following general procedure:
1. Dissolve hydrocodone bitartrate in water to form a 50 mg/mL hydrocodone bitartrate/water solution.
2. Form a slurry by adding AMBERLITE® IRP69 resin to the hydrocodone bitartrate/water solution, while stirring, in an amount such that the weight ratio of ion exchange resin to active agent in the resulting slurry is about 3:1. Continue stirring the slurry for about 1 hour.
3. Combine the slurry with a substrate (i.e., acetaminophen granules) and dry using a fluid bed dryer for about 2 hours to form a hydrocodone-resin-acetaminophen granulation.
4. Optionally blend the resulting hydrocodone-resin-acetaminophen granulation with excipients to form a blend.
5. Compress the resulting blend to form round tablets comprising 5 mg hydrocodone and 300 mg acetaminophen.

Example 9

Exemplary Method for Making Hydrocodone Bitartrate/Acetaminophen Resinate Tablets Tablet compositions comprising an hydrocodone/ion exchange resin complex and acetaminophen were prepared according to the following general procedure:
1. Dissolve hydrocodone bitartrate in water to form, for example, a 50 mg/mL hydrocodone bitartrate/water solution.
2. Add polacrilin potassium resin to the hydrocodone bitartrate/water solution, while stirring, in an amount such that the weight ratio of ion exchange resin to active agent in the resulting suspension is about 3:1. Continue stirring the slurry for at least 2 hours.
3. Load acetaminophen granules (containing 90% acetaminophen and 10% excipients) in a fluid bed granulator.
4. Top-spray the aqueous suspension of hydrocodone bitartrate and polacrilin potassium onto the acetaminophen granules and dry in the fluid bed granulator to form dry acetaminophen particles mixed with hydrocodone/resin (i.e., a hydrocodone-resin-acetaminophen granulation).
5. Optionally blend the hydrocodone-resin-acetaminophen granulation with excipients to form a blend.
6. Compress the resulting blend using a rotary tablet press to form round tablets comprising hydrocodone and acetaminophen.

Example 10

Hydrocodone/Acetaminophen Resinate Tablet Composition Examples

The general procedure set forth in Example 9 was used to prepare tablets comprising: (A) a hydrocodone/ion exchange resin complex equivalent to 5 mg hydrocodone bitartrate and 325 mg acetaminophen; (B) a hydrocodone/ion exchange resin complex equivalent to 7.5 mg hydrocodone bitartrate and 325 mg acetaminophen; and (C) a hydrocodone/ion exchange resin complex equivalent to 10 mg hydrocodone bitartrate and 325 mg acetaminophen, the compositions of which are further described in TABLE 5:

TABLE 5

| Ingredients | COMPOSITION A 5 mg/325 mg Tablet (mg/tablet) | COMPOSITION B 7.5 mg/325 mg Tablet (mg/tablet) | COMPOSITION C 10 mg/325 mg Tablet (mg/tablet) |
|---|---|---|---|
| Hydrocodone bitartrate | 5 | 7.5 | 10 |
| Polacrilin potassium | 15 | 22.5 | 30 |
| Acetaminophen granules (90% acetaminophen; 10% excipients) | 361.12 | 361.12 | 361.12 |
| Microcrystalline cellulose | 111.28 | 101.28 | 91.28 |
| Pregelatinized starch | 27.50 | 27.50 | 27.50 |
| Xanthan gum | 20.50 | 20.50 | 20.50 |
| Colloidal silicon dioxide | 5.50 | 5.50 | 5.50 |
| Magnesium stearate | 4.10 | 4.10 | 4.10 |
| Total Tablet Weight | 550 | 550 | 550 |

Example 11

Comparative Syringeability of Hydrocodone from Hydrocodone/Acetaminophen 10 mg/300 mg Resinate Tablets in Aqueous Solvents Relative to Vicodin®

Reference tablets comprising hydrocodone/acetaminophen 10 mg/300 mg (Vicodin®) were tested for syringeability of hydrocodone bitartrate in the solvents tap water, saline, vinegar and 40% ethanol under both boiling and non-boiling conditions using the same procedure for testing syringeability set forth in Example 5. The results are set forth in TABLE 6. The "% Extracted Hydrocodone Bitartrate" column presents the amount of hydrocodone bitartrate extracted into the syringe relative to the total amount of hydrocodone bitartrate originally in the tablet.

TABLE 6

Syringeability of Hydrocodone Bitartrate and Acetaminophen Tablets, 10 mg/300 mg (Vicodin ®)

| Solvent | Trial | Amt. Aspirated (mL) | % Extracted Hydrocodone Bitartrate |
|---|---|---|---|
| 40% EtOH | 1 | 1.4 | 21 |
| | 2 | 2.2 | 40 |
| 40% EtOH — Boiled | 1 | 1.8 | 30 |
| | 2 | 3.0 | 57 |
| Saline | 1 | 4.4 | 61 |
| | 2 | 3.4 | 76 |
| Saline — Boiled | 1 | <0.1 | 0 |
| | 2 | 3.8 | 68 |
| Tap water | 1 | 2.0 | 33 |
| | 2 | 2.4 | 40 |
| Tap water — Boiled | 1 | 3.4 | 59 |
| | 2 | 4.0 | 71 |
| Vinegar | 1 | 0.8 | 12 |
| | 2 | 3.7 | 67 |
| Vinegar — Boiled | 1 | 4.0 | 67 |
| | 2 | 3.8 | 73 |

Tablets comprising a hydrocodone/ion exchange resin complex equivalent to 10 mg hydrocodone bitartrate and 300 mg acetaminophen prepared using the general procedure set forth in Example 9 were tested for syringeability of hydrocodone bitartrate in the solvents tap water, saline, vinegar and 40% ethanol under both boiling and non-boiling conditions using the same procedure for testing syringeability set forth in Example 5. The results are set forth in TABLE 7.

TABLE 7

Syringeability of Hydrocodone Bitartrate and Acetaminophen Resinate Tablets, 10 mg/300 mg

| Solvent | Trial | Amt. Aspirated (mL) | % Extracted Hydrocodone Bitartrate |
|---|---|---|---|
| 40% EtOH | 1 | <0.1 | 0 |
| | 2 | 0.1 | 0 |
| 40% EtOH — Boiled | 1 | <0.1 | 0 |
| | 2 | 0.1 | 1 |

TABLE 7-continued

Syringeability of Hydrocodone Bitartrate and
Acetaminophen Resinate Tablets, 10 mg/300 mg

| Solvent | Trial | Amt. Aspirated (mL) | % Extracted Hydrocodone Bitartrate |
|---|---|---|---|
| Saline | 1 | 0.2 | 1 |
| | 2 | 0.1 | 1 |
| Saline — Boiled | 1 | <0.1 | 0 |
| | 2 | <0.1 | 0 |
| Tap water | 1 | 0.4 | 1 |
| | 2 | <0.1 | 0 |
| Tap water — Boiled | 1 | <0.1 | 0 |
| | 2 | <0.1 | 0 |
| Vinegar | 1 | 0.2 | 1 |
| | 2 | <0.1 | 0 |
| Vinegar — Boiled | 1 | <0.1 | 0 |
| | 2 | <0.1 | 0 |

Example 12

Comparative Syringeability of Hydrocodone from Hydrocodone/Acetaminophen 10 mg/325 mg Resinate Tablets in Aqueous Solvents Relative to Norco®

Reference tablets comprising hydrocodone/acetaminophen 5 mg/325 mg (Norco®) were tested for syringeability of hydrocodone bitartrate in the 40% ethanol and saline under non-boiling conditions using the same procedure for testing syringeability set forth in Example 5. The results are set forth in TABLE 8.

TABLE 8

Syringeability of Hydrocodone Bitartrate and Acetaminophen Tablets, 5 mg/325 mg (Norco ®)

| Solvent | Trial | Amt. Aspirated (mL) | % Extracted Hydrocodone Bitartrate |
|---|---|---|---|
| 40% EtOH | 1 | 2.2 | 24 |
| | 2 | 3.7 | 42 |
| Saline | 1 | 2.2 | 35 |
| | 2 | 1.5 | 26 |

Tablets comprising a hydrocodone/ion exchange resin complex equivalent to 10 mg hydrocodone bitartrate and 300 mg acetaminophen, prepared in 4 lots using the general procedure set forth in Example 9, were tested for syringeability of hydrocodone bitartrate in the solvents 40% ethanol and saline under non-boiling conditions using the same procedure for testing syringeability set forth in Example 5. The results for Lot 1 are set forth in TABLE 9.

TABLE 9

Syringeability of Hydrocodone Bitartrate and Acetaminophen Resinate Tablets, 10 mg/325 mg, Lot 1

| Solvent | Trial | Amt. Aspirated (mL) | % Extracted Hydrocodone Bitartrate |
|---|---|---|---|
| 40% EtOH | 1 | 0.8 | 9 |
| | 2 | 0.8 | 6 |
| Saline | 1 | 0.3 | 3 |
| | 2 | 0.2 | 4 |

The results for Lot 2 are set forth in TABLE 10.

TABLE 10

Syringeability of Hydrocodone Bitartrate and Acetaminophen Resinate Tablets, 10 mg/325 mg, Lot 2

| Solvent | Trial | Amt. Aspirated (mL) | % Extracted Hydrocodone Bitartrate |
|---|---|---|---|
| 40% EtOH | 1 | 0.3 | 3 |
| | 2 | 0.2 | 1 |
| Saline | 1 | 0.5 | 1 |
| | 2 | 0.1 | 1 |

The results for Lot 3 are set forth in TABLE 11.

TABLE 11

Syringeability of Hydrocodone Bitartrate and Acetaminophen Resinate Tablets, 10 mg/325 mg, Lot 3

| Solvent | Trial | Amt. Aspirated (mL) | % Extracted Hydrocodone Bitartrate |
|---|---|---|---|
| 40% EtOH | 1 | 0.2 | 1 |
| | 2 | 0.4 | 0 |
| Saline | 1 | 0.2 | 4 |
| | 2 | 0.4 | 5 |

The results for Lot 4 are set forth in TABLE 12.

TABLE 12

Syringeability of Hydrocodone Bitartrate and Acetaminophen Resinate Tablets, 10 mg/325 mg, Lot 4

| Solvent | Trial | Amt. Aspirated (mL) | % Extracted Hydrocodone Bitartrate |
|---|---|---|---|
| 40% EtOH | 1 | 0.2 | 0 |
| | 2 | 0.4 | 2 |
| Saline | 1 | 0.2 | 2 |
| | 2 | 0.2 | 2 |

Example 13

Comparative Dissolution Profiles of Hydrocodone Bitartrate and Acetaminophen from Hydrocodone Bitartrate/Acetaminophen 10 mg/325 mg Resinate Tablets in 0.1 N HCl Relative to Norco®

Figure 9:
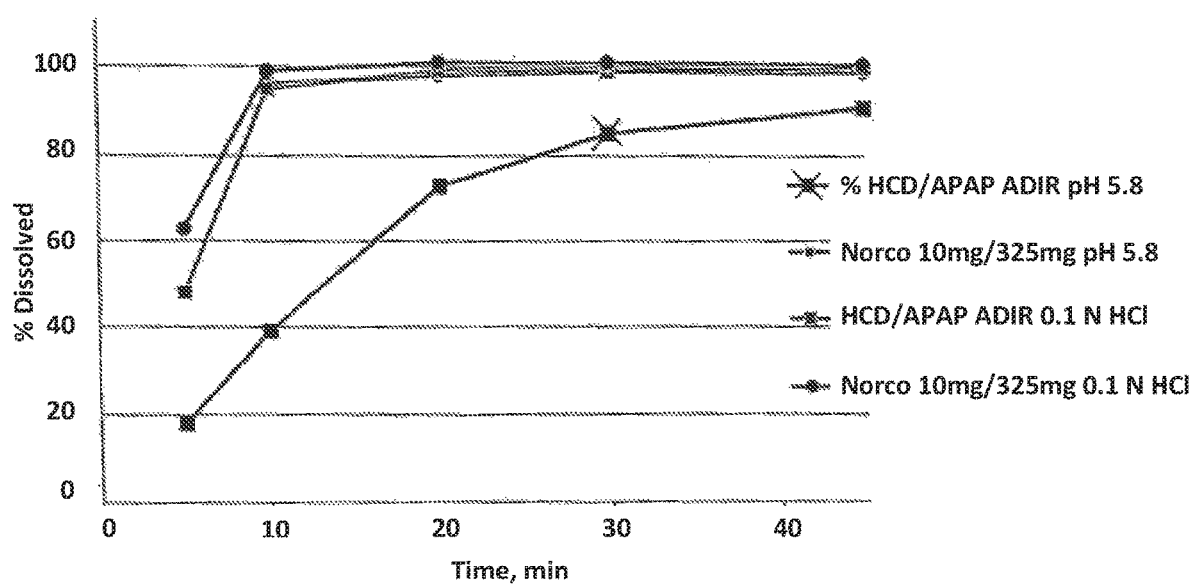
FIG. 9 is a graph presenting acetaminophen dissolution data for an exemplary composition comprising hydrocodone bitartrate, ion exchange material, and acetaminophen as compared to a reference, according to an exemplary embodiment of the present disclosure.
Figure 10:
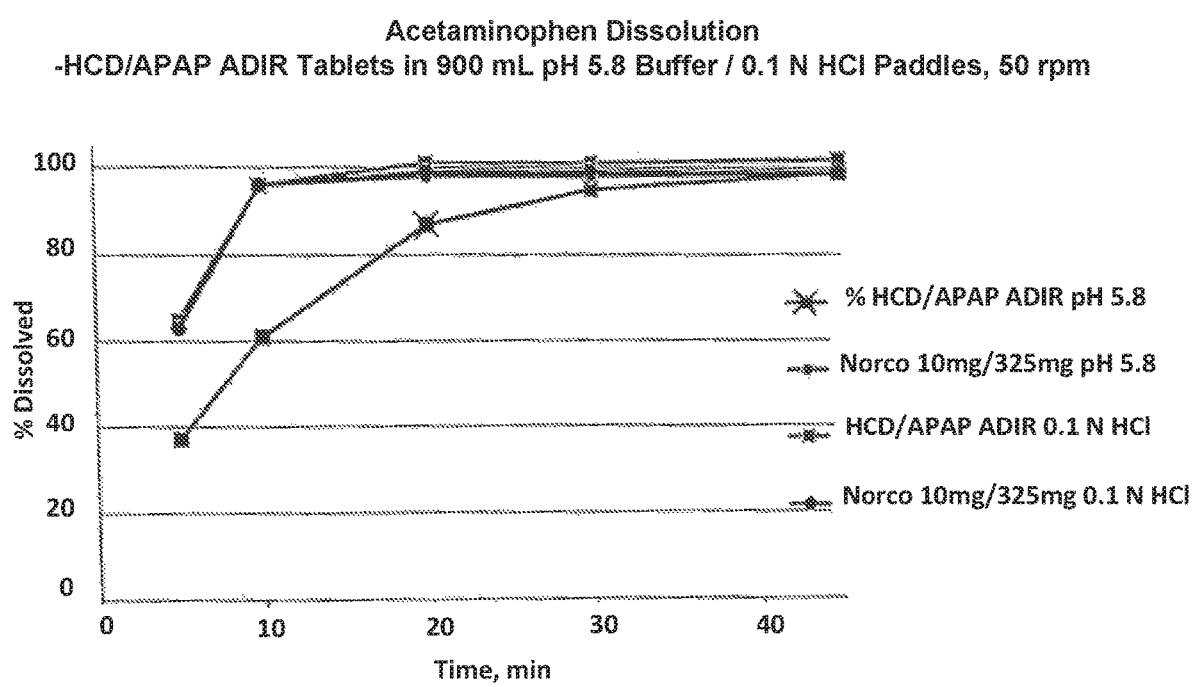
FIG. 10 is a graph presenting hydrocodone bitartrate dissolution data for an exemplary composition comprising hydrocodone bitartrate, ion exchange material, and acetaminophen as compared to a reference, according to an exemplary embodiment of the present disclosure.

Tablets comprising a hydrocodone/ion exchange resin complex equivalent to 10 mg hydrocodone bitartrate and 325 mg acetaminophen prepared using the general procedure set forth in Example 9 were subjected to in-vitro dissolution in 900 ml 0.1 N HCl using a USP Apparatus 2 (paddle) at 50 rpm. The results for acetaminophen as compared to a 10 mg/325 mg hydrocodone/acetaminophen reference (Norco®) are set forth in FIG. 9. The results for hydrocodone bitartrate as compared to a 10 mg/325 mg hydrocodone/acetaminophen reference (Norco®) are set forth in FIG. 10.

Example 14

Exemplary Method for Making Hydrocodone Bitartrate/Acetaminophen Resinate Tablets (Admixture)

Tablet compositions comprising a hydrocodone/ion exchange resin complex and acetaminophen were prepared according to the following general procedure:

1. Mix hydrocodone bitartrate, ion exchange resin, acetaminophen granules, and excipients to form a dry blend or admixture (without granulation).
2. Compress the resulting dry blend or admixture using a rotary tablet press to form tablets comprising hydrocodone and acetaminophen.

Example 15

Hydrocodone/Acetaminophen Resinate Tablet Composition Examples (Admixture)

The general procedure set forth in Example 14 was used to prepare tablets comprising a hydrocodone/ion exchange resin admixture equivalent to 10 mg hydrocodone bitartrate and 300 mg acetaminophen, as further described in TABLE 13:

TABLE 13

| Ingredients | Amount (mg/tablet) |
| --- | --- |
| Hydrocodone bitartrate | 10 |
| Polacrilin resin C115KMR/5100 powder | 30 |
| Acetaminophen granules (90% acetaminophen; 10% excipients) | 333.3 |
| Microcrystalline cellulose | 109.5 |
| Pregelatinized starch | 33.0 |
| Xanthan gum | 24.6 |
| Colloidal silicon dioxide | 5.5 |
| Magnesium stearate | 4.1 |
| Total Tablet Weight | 550 |

Example 16

Syringeability of Hydrocodone from Hydrocodone/Acetaminophen 10 mg/300 mg Resinate Tablets (Admixture) in Aqueous Solvents Tablets of Example 15 were tested for syringeability in the solvents saline and 40% ethanol using the same procedure for testing syringeability set forth in Example 5. The results are set forth in TABLE 14.

TABLE 14

Syringeability of Hydrocodone Bitartrate and Acetaminophen Resinate Tablets, 10 mg/300 mg

| Solvent | Trial | Amt. Aspirated (mL) | % Extracted Hydrocodone Bitartrate |
| --- | --- | --- | --- |
| 40% EtOH | 1 | 0.2 | 3 |
|  | 2 | <0.1 | 1 |
| Saline | 1 | <0.1 | 0 |
|  | 2 | <0.1 | 0 |

Example 17

Comparative Hydrocodone Acetaminophen Tablet Composition (No Ion Exchange Material)

The general procedure set forth in Example 14, except for the step of mixing in an ion exchange resin, was used to prepare tablets having the following composition set forth in TABLE 15:

TABLE 15

| Ingredients | Amount (mg/tablet) |
| --- | --- |
| Hydrocodone bitartrate | 10 |
| Acetaminophen granules (90% acetaminophen; 10% excipients) | 333.3 |
| Microcrystalline cellulose | 139.5 |
| Pregelatinized starch | 33.0 |
| Xanthan gum | 24.6 |
| Colloidal silicon dioxide | 5.5 |
| Magnesium stearate | 4.1 |
| Total Tablet Weight | 550 |

Example 18

Comparative Syringeability of Hydrocodone from Comparative Hydrocodone Acetaminophen Tablet Composition (No Ion Exchange Material) in Aqueous Solvents Tablets of Example 17 were tested for syringeability in the solvents saline and 40% ethanol using the same procedure for testing syringeability set forth in Example 5. The results are set forth in TABLE 16.

TABLE 16

Syringeability of Comparative Hydrocodone Bitartrate and Acetaminophen Tablets (No Ion Exchange Material), 10 mg/300 mg

| Solvent | Trial | Amt. Aspirated (mL) | % Extracted Hydrocodone Bitartrate |
| --- | --- | --- | --- |
| 40% EtOH | 1 | <0.1 | 1 |
|  | 2 | <0.1 | 1 |
| Saline | 1 | <0.1 | 0 |
|  | 2 | <0.1 | 1 |

Example 19

Comparative Dissolution Profiles of Hydrocodone Bitartrate and Acetaminophen from Hydrocodone Bitartrate/Acetaminophen 10 mg/300 mg Resinate Tablets (Admixture) Relative to a Comparative Hydrocodone Acetaminophen Tablet Composition (No Ion Exchange Material) and a Reference (Vicodin®)

Figure 11:
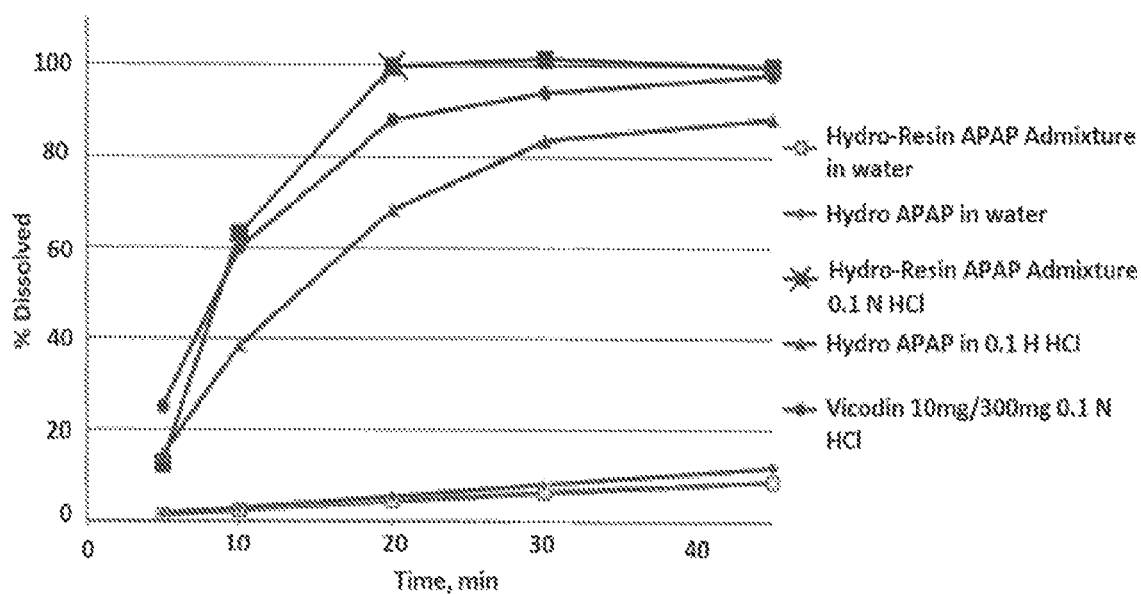
FIG. 11 is a graph presenting hydrocodone bitartrate dissolution data for an exemplary composition comprising acetominaphen and an admixture of hydrocodone bitartrate and ion exchange material, as compared to a reference composition and to a composition comprising hydrocodone bitartrate and acetaminophen without ion exchange material, according to an exemplary embodiment of the present disclosure.
Figure 12:
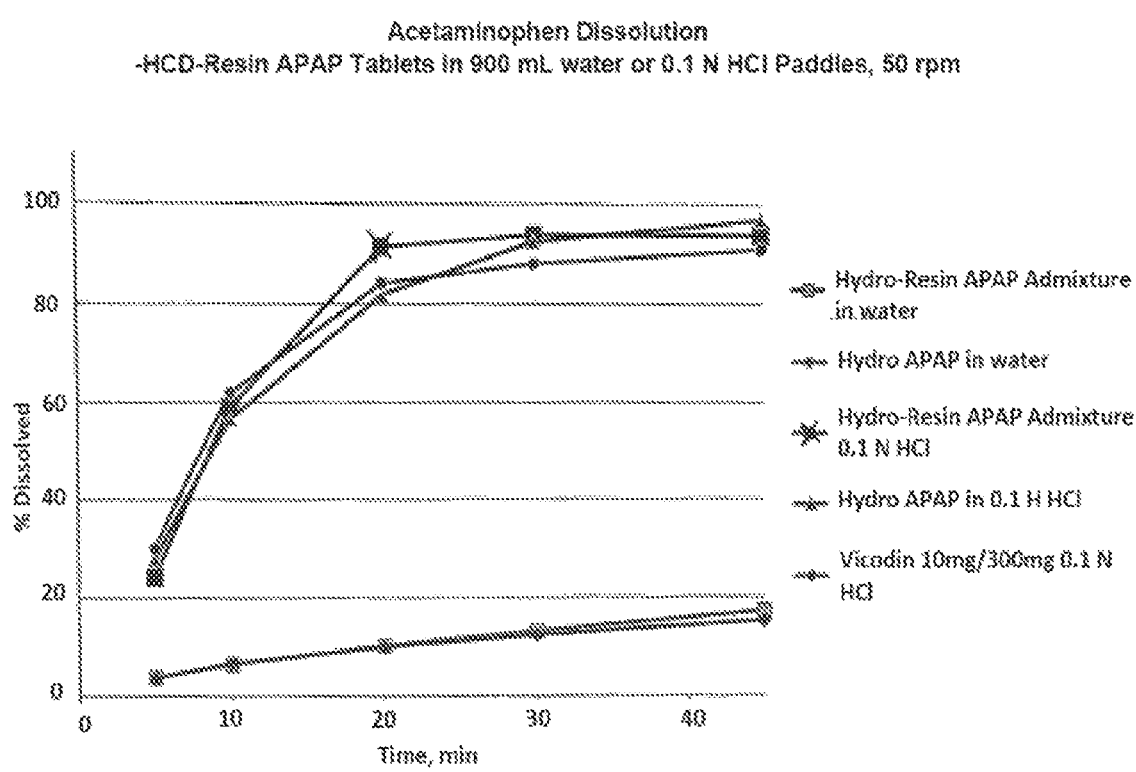
FIG. 12 is a graph presenting acetaminophen dissolution data for an exemplary composition comprising acetaminophen and an admixture of hydrocodone bitartrate and ion exchange material, as compared to a reference composition and to a composition comprising hydrocodone bitartrate and acetaminophen without an ion exchange material, according to an exemplary embodiment of the present disclosure.

Tablets of Example 15 were subjected to in-vitro dissolution in 900 ml of 0.1 N HCl or water using a USP Apparatus 2 (paddle) at 50 rpm. The results for hydrocodone bitartrate as compared to tablets of Example 17 and to a 10 mg/300 mg hydrocodone/acetaminophen reference (Vicodin®) are set forth in FIG. 11. The results for acetaminophen as compared to tablets of Example 17 and a 10 mg/300 mg hydrocodone/acetaminophen reference (Vicodin®) are set forth in FIG. 12.

Example 20

Comparative Dissolution Profiles of Hydromorphone HCl from Hydromorphone HCl 8.0 mg Resinate Tablets (Complex) Relative to a Reference (Dilaudid®)

Hydromorphone HCl resinate tablets containing a complex of the hydromorphone HCl and an ion exchange material were prepared as follows:

1. Hydromorphone HCl was dissolved in 100 g of purified water in a 250 ml beaker while mixing with a magnetic stirrer.
2. Amberlite IRP 69 was added to the solution while mixing, and the mixing continued for about 2 hours.
3. The resulting suspension was added gradually to lactose monohydrate in a Hubart mixer while mixing.
4. The resulting granules were dried in an oven at 60 degree C. until a loss on drying of about 2.0% was achieved.
5. The granules were passed through a screen No. 20 and then mixed with magnesium stearate in a plastic bag for about 2 minutes.
6. Tablets were formed by direct compression at 254 mg tablet weight and 3 to 5 kP hardness.

TABLE 17 lists the amount of each ingredient per unit or its respective percent per tablet.

TABLE 17

| | Hydromorphone HCl 8.0 mg ADIR | mg/unit | %/Tablet |
|---|---|---|---|
| 1 | Hydromorphone HCl | 8.00 | 3.15 |
| 2 | Amberlite IRP 69 | 24.00 | 9.45 |
| 3 | Purified Water | 0.00 | 0.00 |
| 4 | Lactose Monohydrate | 220.00 | 86.61 |
| 5 | Mg. Stearate | 2.00 | 0.79 |
| | Total | 254.00 | 100.00 |

Figure 13:
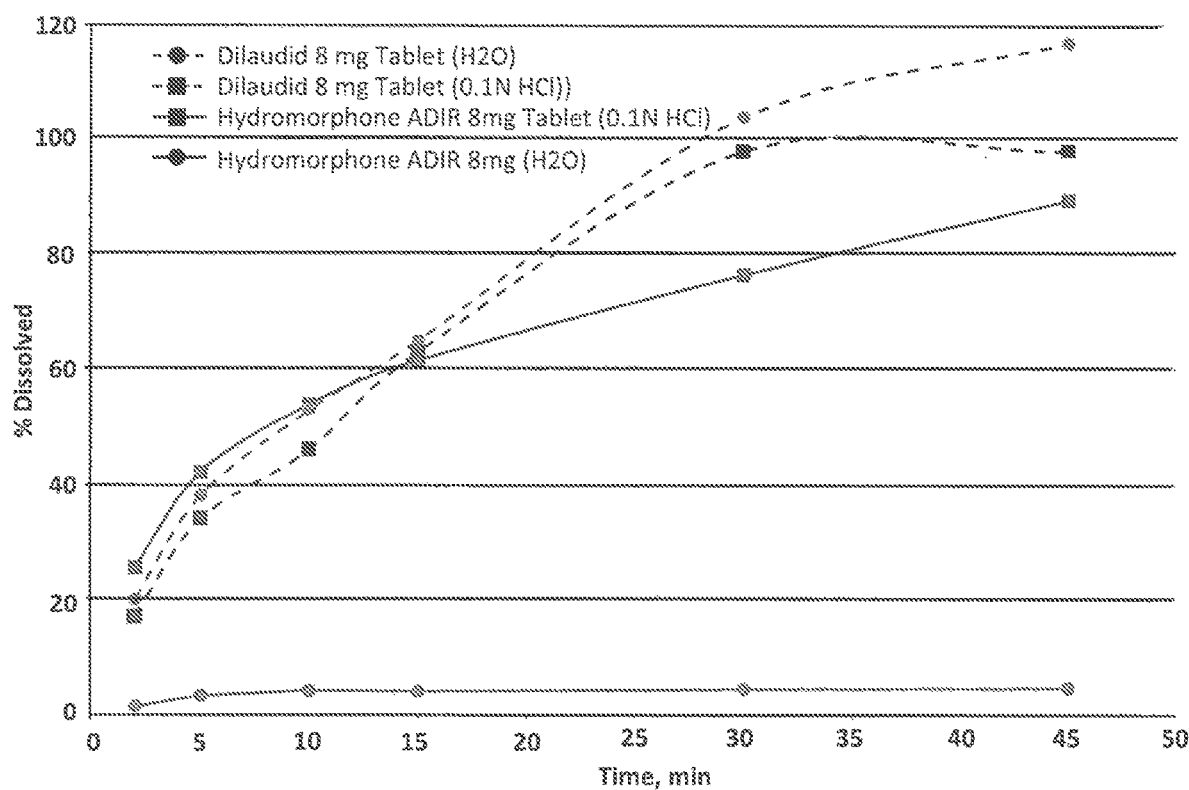
FIG. 13 is a graph presenting hydromorphone dissolution data for an exemplary composition comprising a complex of hydromorphone and an ion exchange material, as compared to a reference material without a complex of hydromorphone and an ion exchange material, according to an exemplary embodiment of the present disclosure.

FIG. 13 is a graph presenting hydromorphone HCl dissolution data for an exemplary composition comprising a complex of hydromorphone HCl and an ion exchange material, as compared to a reference material (i.e., Dilaudid®) without such a complex. As shown in FIG. 13, about 90% of the hydromorphone HCl was released from the hydromorphone HCl resinate tablets according to at least one embodiment described herein at about 45 minutes when dissolved in 0.1 N HCl, whereas less than 10% of hydromorphone HCl was released from such tablets during the same time period when dissolved in water. In comparison, the Dilaudid® tablets release about 99% or more of the hydromorphone HCl within the same time period regardless of the solvent used for the dissolution.

What is claimed is:

1. A pharmaceutical composition comprising:
   a mixture comprising at least one active agent and an ion exchange resin, wherein the mixture is layered over a plurality of cores,
   wherein a weight ratio of the ion exchange resin to the at least one active agent is about 1:1 to about 20:1,
   wherein the composition provides an immediate release and releases about 75% or more of the at least one active agent within about 1 hour as measured by in-vitro dissolution in a USP Apparatus 2 (paddle) at about 50 rpm in about 900 ml 0.1N HCl at about 37° C.,
   wherein the pharmaceutical composition is a compressed tablet comprising the plurality of cores layered with the mixture.

2. The pharmaceutical composition of claim 1, wherein the composition releases about 85% or more of the at least one active agent within about 30 minutes as measured by in-vitro dissolution in a USP Apparatus 2 (paddle) at about 50 rpm in about 900 ml 0.1N HCl at about 37° C.

3. The pharmaceutical composition of claim 1, wherein the composition releases about 20% or less of the at least one active agent within about 45 minutes as measured by in-vitro dissolution in a USP Apparatus 2 (paddle) at about 50 rpm in about 900 ml water at about 37° C.

4. The pharmaceutical composition of claim 1, wherein the composition releases about 20% or less of the at least one active agent within about 45 minutes as measured by in-vitro dissolution in a USP Apparatus 2 (paddle) at about 50 rpm in about 900 ml in 40% ethanol in water v/v at about 37° C.

5. The pharmaceutical composition of claim 1, wherein the active agent comprises an opioid agonist.

6. The pharmaceutical composition of claim 5, wherein the opioid agonist comprises at least one of oxycodone, oxymorphone, hydrocodone, hydromorphone, morphine, codeine, tramadol, tapentadol, fentanyl, and pharmaceutically acceptable salts, hydrates and solvates thereof, or mixtures thereof.

7. The pharmaceutical composition of claim 6, wherein the opioid agonist comprises at least one of oxycodone hydrochloride, hydrocodone bitartrate, or hydromorphone hydrochloride.

8. The pharmaceutical composition of claim 1, further comprising at least one second active agent.

9. The pharmaceutical composition of claim 8, wherein the at least one second active agent comprises a non-opioid analgesic.

10. The pharmaceutical composition of claim 9, wherein the non-opioid analgesic comprises at least one of non-steroidal anti-inflammatory agents or acetaminophen.

11. The pharmaceutical composition of claim 9, wherein the at least one second active agent comprises an antagonist to the active agent.

12. The pharmaceutical composition of claim 11, wherein the antagonist comprises at least one of naltrexone, naloxone, nalmefene, cyclazacine, levallorphan, buprenorphine, pharmaceutically acceptable salts, hydrates and solvates thereof, or mixtures thereof.

13. The pharmaceutical composition of claim 12, wherein the antagonist comprises at least one of naltrexone hydrochloride or naloxone hydrochloride.

14. The pharmaceutical composition of claim 1, wherein the active agent comprises at least one of central nervous system (CNS) stimulants, CNS depressants, tranquilizers, sedative hypnotics, or combinations thereof.

15. The pharmaceutical composition of claim 1, further comprising at least one abuse deterrent agent comprising one or more of at least one gelling agent, at least one bittering agent, or at least one irritant.

16. The pharmaceutical composition of claim 15, wherein the at least one gelling agent comprises at least one of sugars, sugar derived alcohols, starch, starch derivatives, cellulose derivatives, attapulgites, bentonites, dextrins, alginates, carrageenan, gums, pectins, gelatin, kaolin, lecithin, magnesium aluminum silicate, carbomers, carbopols, polyvinylpyrrolidone, polyethylene glycol, polyethylene oxide, polyvinyl alcohol, silicon dioxide, curdlan, furcelleran, egg white powder, lacto albumin, soy protein, chitosan, surfactants, emulsifiers, and pharmaceutically acceptable salts thereof or mixtures thereof.

17. The pharmaceutical composition of claim 1, wherein the ion exchange resin is present in an amount of about 2.5 mg to about 15,000 mg.

18. The pharmaceutical composition of claim 1, wherein the mixture comprises the at least one active agent and the ion exchange resin in an admixture.

19. The pharmaceutical composition of claim 1, wherein the mixture comprises a complex of the at least one active agent and the ion exchange resin.

20. The pharmaceutical composition of claim 19, wherein the mixture comprises about 25% or more of the complex.

21. The pharmaceutical composition of claim 1, wherein the at least one active agent comprises about 2.5 mg to about 10 mg oxycodone or a pharmaceutically acceptable salt thereof, or comprises about 2.5 mg to about 15 mg of hydrocodone or a pharmaceutically acceptable salt thereof.

22. The pharmaceutical composition of claim 7, wherein the oxycodone hydrochloride has a 14-hydroxycodeinone level of less than about 25 ppm.

23. The pharmaceutical composition of claim 1, wherein the substrate comprises a non-opioid analgesic.

24. A pharmaceutical composition comprising:
- a mixture comprising at least one active agent and an ion exchange resin, wherein the mixture is layered over a plurality of substrates, wherein the plurality of substrates is free of an osmotic agent,
- wherein a weight ratio of the ion exchange resin to the at least one active agent is about 1:1 to about 20:1,
- wherein the composition provides an immediate release and releases about 75% or more of the at least one active agent within about 1 hour as measured by in-vitro dissolution in a USP Apparatus 2 (paddle) at about 50 rpm in about 900 ml 0.1N HCl at about 37° C.,
- wherein the pharmaceutical composition is a compressed tablet comprising the plurality of substrates layered with the mixture.

* * * * *